United States Patent [19]

Corbier et al.

[11] Patent Number: 5,714,508
[45] Date of Patent: Feb. 3, 1998

[54] BICYCLE DERIVATIVES OF IMIDAZOLE

[75] Inventors: Alain Corbier, Verrieres le Buisson; Jean Paul Vevert, Pantin; Jidong Zhang, Paris, all of France

[73] Assignee: Roussel Uclaf, France

[21] Appl. No.: 283,984

[22] Filed: Aug. 1, 1994

[30] Foreign Application Priority Data

Aug. 5, 1993 [FR] France ................. 93 09654

[51] Int. Cl.$^6$ ............ A61K 31/415; C07D 235/02
[52] U.S. Cl. ............... 514/393; 514/394; 514/395; 548/303.1
[58] Field of Search ............ 548/303.1; 514/393, 514/394, 395

[56] References Cited

U.S. PATENT DOCUMENTS

| | | | |
|---|---|---|---|
| 5,157,026 | 10/1992 | Chakravarty et al. | 514/81 |
| 5,338,756 | 8/1994 | Fortin et al. | 514/394 |

FOREIGN PATENT DOCUMENTS

| | | |
|---|---|---|
| 2078058 | 3/1993 | Canada. |
| 0461040 | 12/1991 | European Pat. Off.. |
| 0503162 | 9/1992 | European Pat. Off.. |
| 0533058 | 3/1993 | European Pat. Off.. |

Primary Examiner—Johann Richter
Assistant Examiner—Laura L. Stockton
Attorney, Agent, or Firm—Bierman, Muserlian and Lucas LLP

[57] ABSTRACT

Described herein are compounds of the formula

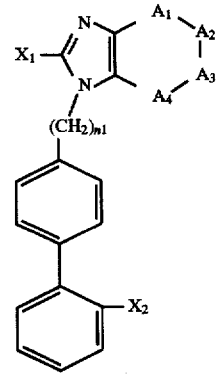

I wherein the substituents are defined as in the specification having inhibiting activity on the effects of angiotensin II.

8 Claims, No Drawings

BICYCLE DERIVATIVES OF IMIDAZOLE

OBJECTS OF THE INVENTION

It is of the invention to provide the novel imidazoles of formula I and their non-toxic, pharmaceutically acceptable salts and a process and intermediates for their preparation.

It is another object of the invention to provide novel compositions and method for inhibiting the effects of angiotensin II.

These and other objects and advantages of the invention will become obvious from the following detailed description.

THE INVENTION

The novel compounds of the invention are selected from the group consisting of a compound of the formula

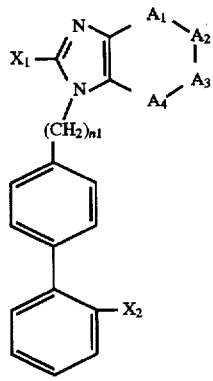

wherein $X_1$ is selected from the group consisting of alkyl, alkenyl, alkynyl, alkoxy and alkylthio of up to 6 carbon atoms, all not interrupted or interrupted by at least one heteroatom selected from the group consisting of oxygen, nitrogen and sulfur and optionally substituted, $n_1$ is an integer from 0 to 4, $A_1$, $A_2$, $A_3$ and $A_4$ are individually selected from the group consisting of —(CH$_2$)$_n$—, —CH=, —NH—, >C=R$_3$, —S— and —O— with the proviso that n is an integer from 0 to 2, at least one of the hydrogens of —(CH$_2$)$_n$—, —CH= and NH— is optionally substituted by one or two identical or different $R_1$ and $R_2$ selected from the group consisting of halogen, hydroxyl, free, salified or esterified carboxy, formyl, acyl, mercapto, amino and acylamino in which the amino is optionally substituted by one or two alkyl, alkenyl, alkoxy and alkylthio of up to 6 carbon atoms and optionally substituted, phenyl, benzyl, phenethyl and phenoxy in which the phenyl is optionally substituted, $R_3$ is selected from the group consisting of oxygen, optionally substituted alkenyl and =N—OR$_4$, $R_4$ is selected from the group consisting of hydrogen, optionally substituted alkyl, alkenyl, acyl and carbamoyl, $X_2$ is selected from the group consisting of cyano, free, salified or esterified carboxy, —SO$_2$—NH$_2$, —SO$_3$R$_7$ in which $R_7$ is hydrogen or alkyl of 1 to 6 carbon atoms, —NH—(CH$_2$)$_{n2}$—SO$_2$—(Z)$_{n4}$R$_5$, in which n2 and n4 individually are 0 or 1, —(CH$_2$)$_{n2}$—SO$_2$—Z—R$_5$, in which Z is selected from the group consisting of —NH—, —NH—CO—, —NH—CO—O—,

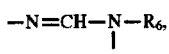

—NH—CO—NH, or a single bond and $R_5$ and $R_6$ are individually selected from the group consisting of hydrogen, alkyl or alkenyl of up to 6 carbon atoms, pyridyl, phenyl, benzyl, nitropyridyl, pyrimidyl, tetrazolyl, diazolyl, piperidyl, alkylpiperidyl, thiazolyl, alkythiazolyl, tetrahydrofuranyl, methyltetrahydrofuranyl, amino and carbamoyl optionally substituted by one or two members of the group consisting of —(CH$_2$)$_{n2}$—SO$_2$—Z—R$_5$ as defined above and alkyl and alkenyl of up to 6 carbon atoms and optionally substituted; all the alkyl, alkenyl alkoxy, alkylthio, phenyl, benzyl, phenethyl and phenoxy being optionally unsubstituted or substituted with at least one member of the group consisting of halogen, hydroxyl, nitro, alkyl, alkenyl and alkoxy of up to 4 carbon atoms, trifluoromethyl, cyano, amino, mono and dialkylamino, free, salified or esterified carboxy, phenyl, pyridyl and tetrazolyl; the products of formula I being in all possible racemic, enantiomeric and diastereoisomeric isomer forms, and their non-toxic, pharmaceutically acceptable salts with acids and bases.

The sulfur atom in the compounds of formula I can be oxidized to the sulfoxide or sulfonic form.

Examples of alkyl are methyl, ethyl, n-propyl, isopropyl, n-butyl, isobutyl, sec-butyl and tert-butyl but can also be pentyl or hexyl and particularly isopentyl and isohexyl. Examples of alkenyl are preferably vinyl, allyl, 1-propenyl, butenyl and preferably buten-1-yl, or pentenyl and examples of alkynyl preferably are ethynyl, propargyl, butynyl or pentynyl.

The halogen is preferably chlorine, but can also be fluorine, bromine or iodine. The acyl of 2 to 6 carbon atoms preferably is acetyl, propionyl, butyryl or benzoyl, but can also be valeryl, hexanoyl, acryloyl, crotonoyl or carbamoyl. The acylamino is preferably one of the acyls as defined above and linked to an oxygen atom such as acetylamino, propionylamino, butyrylamino, valerylamino, carbamoylamino and benzoylamino.

The esterified carboxy is preferably a lower alkoxy carbonyl such as methoxycarbonyl, ethoxycarbonyl, tert-butoxycarbonyl or benzyloxycarbonyl.

The alkoxy is preferably methoxy or ethoxy, but can also be propoxy, isopropoxy, linear, secondary or tertiary butoxy and the alkylthio have the alkyl as indicated above for alkyl and the alkylthio is preferably methylthio or ethylthio, but can also be propylthio, isopropylthio, n-butylthio, sec-butylthio, tert-butylthio, isopentylthio or isohexylthio.

The alkylpiperidyl and alkylthiazolyl are groups in which the alkyl can have the values defined above such as methylpiperidyl, dimethylpiperidyl, trifluoromethylpiperidyl and methylthiazolyl, it being understood that in the non-exhaustive list above, methyl can be replaced just as equally by ethyl, propyl or butyl.

Phenylvinyl or phenylallyl can also be mentioned, it being understood that in these the phenyl can be replaced just as equally by the pyridyl or tetrazolyl.

The alkyl, alkenyl, alkynyl, alkoxy, alkylthio, phenyl, benzyl, phenethyl and phenoxy as defined above can not be substituted or can carry one or more substituents selected from the group consisting of halogen such as chloro or bromo, as in 2-bromoethyl; hydroxyl; cycloalkyl, for example cyclopropyl, cyclopentyl or cyclohexyl; optionally substituted cycloalkenyl, for example cyclohexenyl as in 1,3-dimethyl-cyclohexene; alkoxy, for example methoxy, ethoxy, n-propoxy or iso-propoxy such as methoxymethyl or 1-ethoxyethyl; substituted alkoxy such as trihaloalkoxy such as trifluoromethoxy; phenoxy; benzyloxy; mercapto; alkylthio, for example, methylthio or ethylthio; substituted alkylthio such as trihaloalkylthio as trifluoromethylthio; arylthio; aralkylthio; amino such as 2-aminoethyl; amino substituted by one or two members selected from the group consisting of alkyl, alkenyl, phenyl and phenethyl as defined above such as monoalkylamino, for example, methylamino or ethylamino; dialkylamino, for example, dimethylamino; nitro; cyano; azido; carboxy; esterified carboxy, for example, methoxycarbonyl or ethoxycarbonyl; formyl; acyl, for example acetyl, propionyl or benzoyl; acyl substituted for example by an amino as defined above or by a cyclic linked to the acyl by a nitrogen atom, this cyclic being able to contain optionally one or more heteroatoms chosen from nitrogen, oxygen or sulfur and as defined above; acyloxy, for example acetoxy or propionyloxy; carbamoyl; substituted carbamoyl for example a lower N-monoalkyl-carbamoyl, such as N-methylcarbamoyl, N-ethylcarbamoyl, a lower N,N-dialkyl carbamoyl such as N,N-dimethylcarbamoyl, N,N-diethylcarbamoyl; N-(lower hydroxyalkyl) carbamoyl such as N-(hydroxymethyl)-carbamoyl, N-(hydroxyethyl)-carbamoyl, a lower carbamoylalkyl such as carbamoylmethyl, carbamoylethyl; phthalimido;acylamido for example acetamido or benzamido; alkoxycarbonylamino for example methoxycarbonylamino or ethoxycarbonylamino; benzyloxycarbonylamino.

Carbamoyl means the non-substituted carbamoyl or the substituted carbamoyl for example a lower N-monoalkyl carbamoyl such as N-methylcarbamoyl, N-ethylcarbamoyl; a lower N,N-dialkyl carbamoyl such as N,N-dimethylcarbamoyl, N,N-diethylcarbamoyl; an N-(lower hydroxyalkyl) carbamoyl such as N-(hydroxymethyl) carbamoyl, N-(hydroxyethyl) carbamoyl, a lower carbamoylalkyl such as carbamoylmethyl or carbamoylethyl.

The amino that can be represented or carried by one or more of the groups defined above and in what follows are groups in which two identical or different groups linked to the nitrogen atom are selected from the group consisting of hydrogen; alkyl as defined above to give preferably monoalkyl- or dialkylamino in which the alkyl contains 1 to 6 carbon atoms in particular methyl, ethyl, isopropyl, trifluoromethyl, pentafluoroethyl, hydroxymethyl, hydroxyethyl, methoxymethyl, methoxyethyl, ethoxyethyl; alkenyl as defined above and preferably vinyl and allyl; phenyl, tetrazolyl, benzyl, phenethyl, naphthyl, indolyl, indolinyl, thienyl, furyl, pyrrolyl, pyridyl, pyrrolidinyl, piperidino, morpholino, piperazinyl, these groups being able to be substituted by one or more groups such as methylpiperazinyl, fluoromethylpiperazinyl, ethylpiperazinyl, propylpiperazinyl, phenylpiperazinyl or benzylpiperazinyl.

The above groups represent for example and in a non-exhaustive manner, —NH-aryl such as —NH-phenyl or —NH-tetrazolyl; —NH-alkyl; —N-(alkyl)$_2$; —NH—CO—NH-alkyl such as —NH—CO—NH—tBu; —NH—CO—NH—n-propyl; NH—CO—NH-aryl such as —NH—CO—NH-tetrazolyl or —NH—CO—NH-pyridyl or —N(alkyl)-CO—NH-tetrazolyl, it being understood that in all these, the alkyl can have the values indicated above and can be optionally substituted as indicated above.

When the groups linked to the nitrogen form with the nitrogen to which they are attached a heterocycle, it may be pyrrolyl, imidazolyl, pyridyl, pyrazinyl, pyrimidyl, indolyl, indolinyl, purinyl, quinolyl, pyrrolidinyl, piperidyl, piperidino, morpholino, or piperazinyl ring. These groups can be optionally substituted by the substituents already mentioned and in particular by one or more selected from the group consisting of chlorine, fluorine, methyl, ethyl, isopropyl, tert-butyl, methoxy, ethoxy, propoxy, benzoyl, methoxycarbonyl and ethoxycarbonyl such as methylpiperazinyl, ethylpiperazinyl, propylpiperazinyl, phenylpiperazinyl or benzylpiperazinyl. In these last two, the phenyl and benzyl can be substituted as indicated previously.

The —(CH$_2$)$_{n2}$—SO$_2$—Z—R$_5$ that can be represented in particular by X$_2$, can have the groups in which (CH$_2$)$_{n2}$ is the value of alkylene derived from alkyls indicated above such as methylene, ethylene, n-propylene or butylene and R$_5$ can be alkyl or alkenyl chosen from the values defined above or phenyl, pyridyl, biphenyl, naphthyl.tetrazolyl. The alkyl or alkenyl represented by R$_5$ can optionally be substituted by phenyl and form in particular benzyl or phenethyl.

These alkyl, alkenyl, phenyl, benzyl and phenethyl can themselves be substituted as indicated above for these groups. Among the substituents that can be carried by R$_5$ when it is alkyl, alkenyl, phenyl, benzyl or phenethyl are the following —PO$_3$H, —PO(OH)Alkyl, —PO(OH)aryl, —PO(OH)Alkoxy, amino, mono- or dialkylamino, free, esterified or salified carboxy, nitro, halogen, alkylthio, alkoxy, hydroxy or mercapto.

The groups represented by X$_2$ can be mentioned by way of example and in a non-exhaustive fashion:

—SO$_3$H, —SO$_3$—CH$_3$, —SO$_3$—CH$_2$—CH$_3$,

—SO$_2$—NH$_2$, —SO$_2$—NH—CH$_3$, —SO$_2$—NH—CF$_3$, —SO$_2$—NH—C$_6$H$_5$,

—SO$_2$—NH-tetrazolyl ,

—SO$_2$—NH—CH$_2$—C$_6$H$_5$,

—CH$_2$—SO$_2$—NH$_2$, —CH$_2$—SO$_2$—NH-C$_6$H$_5$, —SO$_2$—NH—CO—NH-alkyl,

—SO$_2$—NH—CO—NH—CH$_3$, —SO$_2$—NH—CO—NH—C$_6$H$_5$, —SO$_2$—NH—CO—NH—tBu

—SO$_2$—NH—CO—NH—CF$_3$, —SO$_2$—NH—CO—NH—CH$_2$—C$_6$H$_5$,

—SO$_2$—NH—CO—NH—C$_6$H$_4$Cl, —SO$_2$—NH—CO—NH-tetrazolyl,

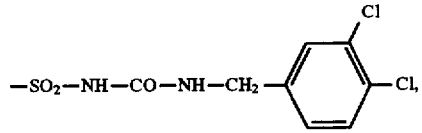

—SO$_2$—NH—CO—NH—CH=CH—CH$_3$,

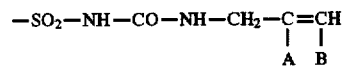

in which A and B individually are chosen from hydrogen, phenyl, pyridyl and pyridinyl,

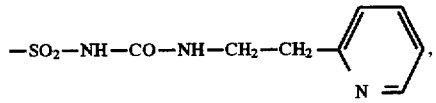

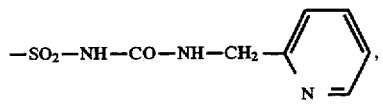

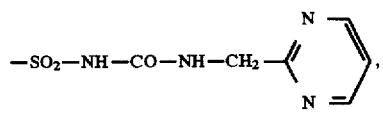

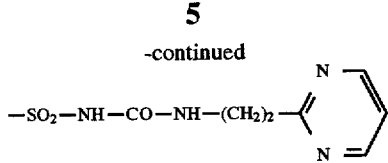

$X_2$ can be chosen from —NH—$(CH_2)n$—$SO_2$—Z—$R_5$ and —CO—NH—$(CH_2)_{n1}$—$SO_2$—Z—$R_5$ in which the $(CH_2)_{n1}$—$SO_2$—Z—$R_5$ can take for example the values indicated above.

$X_2$ can also be free, esterified or salified carboxy, cyano or formyl or tetrazolyl, tetrazolylalkyl, preferably tetrazolylethyl or tetrazolylcarbamoyl.

The following radicals can be mentioned by way of example and in a non-exhaustive manner:

—$SO_2$—NH—$SO_2$-tetrazolyl,

—$SO_2$—NH—$SO_2$—$NH_2$; —$SO_2$—NH—$SO_2$—NH (tBu ),

—$SO_2$—NH—$SO_2$—tBu, and also, as non-exhaustive examples,

—NH-(alkyl), —NH-aryl, —NH-tetrazolyl, —$SO_2$—NH—$CO_2$-alkyl, —$SO_2$—NH—$CO_2$-aryl, —$SO_2$—NH—$CO_2$-tetrazolyl, —NH—CO—NH-aryl, —NH—CO—NH-tetrazolyl, —$CO_2$—NH—$CO_2$-aryl, —$CO_2$—NH—$CO_2$-tetrazolyl, —$CO_2$—NH—$SO_2$—O-aryl, $CO_2$—NH—$SO_2$—N(alk)$_2$, —$CO_2$—NH—$SO_2$—N,

—NH—$SO_2$—$CH_3$, —NH—$SO_2$—$C_6H_5$, —NH—$SO_2$—$CF_3$,

—NH—$CH_2$—$SO_2$—NH—$C_6H_5$,

—CO—NH—$SO_2$—$C_2H_5$, —CO—NH—$SO_2$—$CH_3$,

—CO—NH—$SO_2$—$CH_2$—$C_6H_5$.

Examples of acids for the formation of the non-toxic, pharmaceutically acceptable acid addition salts are hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as methanesulfonic acid, ethanesulfonic acid, propanesulfonic acid, alkyldisulfonic acids such as methanedisulfonic acid, α,β-ethanedisulfonic acid, arylmonosulfonic acids such as benzenesulfonic acid and aryldisulfonic acids.

The carboxy of the products of formula I can be salified by mineral bases such as an equivalent of sodium, potassium, lithium, calcium, magnesium or ammonium or organic bases such as methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine and N-methylglucamine.

A particular subject of the invention is the products having the formula

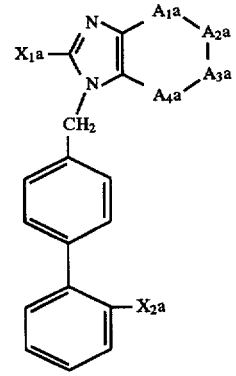

Ia wherein $X_1a$ is alkyl of 1 to 6 carbon atoms, $A_1a$, $A_2a$, $A_3a$ and $A_4a$ are individually selected from the group consisting of —$(CH_2)_{n1a}$—, —CH=, —N=, —NH—, >C=O, >C=N—OH, >C=N—O—$(CH_2)_{n3}$—COOH, >C=CH—COOH,

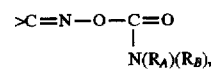

—S— and —O— such that: n1a and n3 are individually 1 or 2, $R_A$ and $R_B$ are individually hydrogen or optionally substituted alkyl, one or more of the hydrogens of —$(CH_2)_{n1a}$— and CH= are optionally substituted by one or two $R_1a$ and $R_2a$ selected from the group consisting of halogen, hydroxyl, free, salified or esterified carboxy, formyl, amino, mono- and dialkylamino, alkyl, alkoxy and alkylthio of up to 6 carbon atoms, $X_{2a}$ is selected from the group consisting of cyano, free, salified or esterified carboxy, optionally salified or esterified tetrazolyl, —$SO_2$—$NH_2$, —$SO_3R_7$ in which $R_7$ is hydrogen or alkyl of 1 to 6 carbon atoms, —NH—$(CH_2)_{n2}$—$SO_2$—$(Z)_{n4}$—$R_5a$ in which n2 and n4 are individually 0 or 1, —$SO_2$—Z—$R_5a$ in which Z is selected from the group consisting of —NH—, —NH—CO—, —NH—CO—O—,

—NH—CO—NH— and a single bond and $R_5a$ and $R_6a$ are individually selected from the group consisting of hydrogen, methyl, ethyl, propyl, vinyl, allyl, pyridyl, phenyl, benzyl, pyridylmethyl, pyridylethyl, nitropyridyl, pyrimidyl, tetrazolyl, diazolyl, piperidinyl, alkylpiperidinyl, thiazolyl, alkylthiazolyl, tetrahydrofuranyl, methyltetrahydrofuranyl, amino or carbamoyl optionally substituted by one or two members of the group consisting of —$SO_2$—Z—$R_5$ as defined above and methyl, ethyl, propyl, vinyl, allyl and trifluoromethyl, the said products of formula Ia being in all possible racemic, enantiomeric and diastereoisomeric isomer forms and their non-toxic, pharmaceutically acceptable salts with acids or bases.

Another particular subject of the invention is the products having the formula

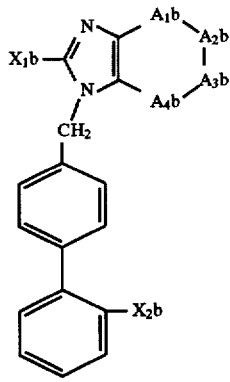

wherein X₁b is selected from the group consisting of methyl, ethyl, propyl, n-butyl, i-butyl or tert-butyl, A₁b is —S— or —CH₂— with one or both of the hydrogen atoms optionally substituted by one or two alkyls of 1 to 4 carbon atoms, and optionally substituted by halogen, hydroxyl, formyl or free, salified or esterified carboxy, A₂b is selected from the group consisting of —(CH₂)$_{n1b}$— with n1b being 1 or 2, —CH=, —S— or —S—CH₂ with one or both of the hydrogens optionally substituted by one or two alkyl of 1 to 4 carbon atoms optionally substituted by halogen, hydroxyl, formyl, free, salified or esterified carboxy, A₃b is selected from the group consisting of —CH₂— or —CH= with a hydrogen being optionally substituted by halogen, formyl or free, salified or esterified carboxy, —NH—, —N= and >C=O, A₄b is selected from the group consisting of >C=O, >C=N—O—CH₂—COOH, >C=N—OH, >C=CH—COOH,

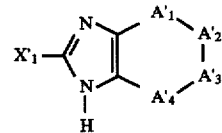

—N=, —NH—, —CH₂— and —CH= with one or both of the hydrogen atoms optionally substituted by one or two individual members of the group consisting of amino, free, salified or esterified carboxy, hydroxyl and halogen, X₂b is selected from the group consisting of optionally salified or esterified tetrazolyl, —SO₂—NH₂, —SO₂—NH—CO—O—R₅b, —SO₂—N=CH—NR₆b, —SO₂—NH—CO—R₅b, —SO₂—NH—CO—NH—R₅b in which R₅b and R₆b are individually selected from the group consisting of hydrogen, methyl, ethyl and n-propyl, the said products of formula Ib being in all possible racemic, enantiomeric and diastereoisomeric isomer forms and their non-toxic, pharmaceutically acceptable addition salts with acids or bases.

Among the specific preferred products of the invention are 4'-[(2-butyl-7-oxo-1,5,6,7-tetrahydro-thiopyrano[2,3-d]-imidazol-1-yl)-methyl]-N-[(dimethylamino)-methylene]-(1,1'-biphenyl)-2-sulfonamide 4'-[(2-butyl-7-oxo-1,5,6,7-tetrahydro-thiopyrano[2,3-d]-imidazol-1-yl)-methyl]-(1,1'-biphenyl)-2-sulfonamide ethyl (2-(4'-((2-butyl-1,5,6,7-tetrahydro-7-oxo-thiopyrano[2,3-d]-imidazol-1-yl)-methyl)-(1,1'-biphenyl)-sulfonyl)-carbamate N-(2-(4'-((2-butyl-1,5,6,7-tetrahydro-7-oxo-thiopyrano{2,3-d]imidazol-1-yl)-methyl)-(1,1'-biphenyl)-sulfonyl)-N'-propylurea.

4'-[(2-butyl-7-(hydroxyimino)-1,5,6,7-tetrahydro-thiopyrano-[2,3-d]-imidazol-1-yl)-methyl]-(1,1'-biphenyl)-2-sulfonamide 4'-[(2-butyl-7-((((propylamino) carbonyl)-oxy)-imino)-1,5,6,7-tetrahydro-thiopyrano[2,3-d]-imidazol-1-yl)-methyl]-N-[(propylamino)-carbonyl]-(1,1'-biphenyl)-2-sulfonamide 4'-[(2-butyl-7-(hydroxyimino)-1,5,6,7-tetrahydro-thiopyrano-[2,3-d]-imidazol-1-yl)-methyl]-N-((propylamino)-carbonyl-(1,1,'-biphenyl)-2-sulfonamide 4'-[(2-butyl-1,7-dihydro-7-oxo-thiopyrano[2,3-d]-imidazol-1-yl)-methyl]-N-[(dimethylamino)-methylene)-(1,1,'-biphenyl)-2-sulfonamide 4'[(2-butyl-1,7-dihydro-7-oxo-thiopyrano[2,3-d]-imidazol-1-yl)-methyl]-(1,1'-biphenyl)-2-sulfonamide and 4'-[(2-butyl-1,7-dihydro-7-oxo-thiopyrano[2,3-d]-imidazol-1-yl)-methyl-N-[(propylamino)-carbonyl]-(1,1,'-biphenyl)-2-sulfonamide.

The process for the preparation of the products of formula I comprises reacting a compound of the formula

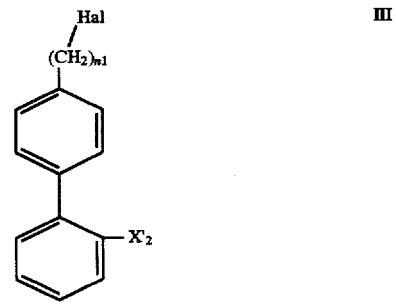

wherein X'₁, A'₁, A'₂, A'₃ and A'₄ have the meanings above for X₁, A₁, A₂, A₃ and A₄ respectively, in which the optional reactive functions are optionally protected by protector groups with a compound of the formula

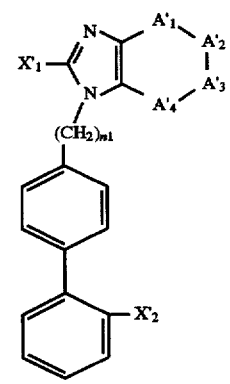

in which Hal is halogen, n1 is an integer from 0 to 4 and X'₂ has the meaning indicated above for X₂ in which the optional reactive functions are optionally protected by protector groups to obtain a product of the formula

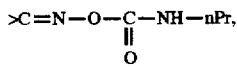

in which X'₁, A'₁, A'₂, A'₃, A'₄ X'₂ and n1 have the meanings indicated above, which product of formula IV can already constitute a product of formula I, and which optionally, is converted to obtain another product of formula I or product of formula IV which is converted into a product of formula I by subjecting the product of formula IV or this product of formula I, optionally and if necessary, to one or more of the following reactions in any order:

elimination of the protector groups that can be carried by the protected reactive functions, salification by a mineral or organic acid or by a mineral or organic base to obtain the corresponding salt, esterification of the acid function, saponification of the ester function into an acid function, conversion of the alkoxy function into hydroxyl, conversion of cyano into an acid, reduction of the carboxy into an alcohol, oxidation of the sulfur atom into the sulfoxide or the sulfone, conversion of the ketone function into an oxime function, conversion of the ketone function into an alcohol function, conversion of the amine function into an amide function, substitution by halogen, resolution of the racemic forms, the said products of formula I thus obtained being in all the possible racemic, enantiomeric and diastereoisomeric isomer forms.

In the preferred process, the product of formula IV can be obtained by reaction of the product of formula III on the free amine function of the product of formula II. This condensation reaction of the products of formula II with a compound of formula III in which the halogen preferably is bromine can be carried out, for example, in an organic solvent such as dimethylformamide or tetrahydrofuran. Thus, the halogenated derivative can be condensed on the anion of the imidazole of formula II prepared for example by the action of a strong base such as sodium or potassium hydride or also of a sodium or potassium alcholoate such as sodium methylate or potassium carbonate in dimethylformamide.

As indicated above, according to the values of $X'_1$, $A'_1$, $A'_2$, $A'_3$, $A'_4$, $R'_1$, $R'_2$, $X'_2$ and n1 the products of formula IV constitute or do not constitute products of formula I, which can be optionally converted into other products of formula I.

The various reactive functions that can be carried by some of the compounds of the reactions defined above can, if necessary, be protected. They can be for example hydroxyl, acyl, free carboxy or also amino and monoalkylamino which can be protected by the appropriate protector groups.

The following non-exhaustive list of examples of protection of the reactive functions can be mentioned:

The hydroxyl can be protected for example by alkyl, trimethylsilyl, dihydropyran, methoxymethyl or tetrahydropyrannyl and the amino groups can be protected for example by acetyl, trityl, benzyl, tert-butoxycarbonyl or phthalimido or other groups known in the chemistry of the peptides.

The acyl groups such as formyl can be protected for example in the form of cyclic or non-cyclic ketals such as dimethyl- or diethylketal or ethylene dioxyketal. The acid functions of the products can be optionally amidified by a primary or secondary amine for example in methylene chloride in the presence of 1-ethyl-3-(dimethylaminopropyl) carbodiimide hydrochloride at ambient temperature. The acid functions can be protected for example in the form of esters formed with easily cleavable esters such as benzylic or terbutylic esters or esters known in the chemistry of the peptides.

The elimination of these protector groups is carried out under the usual conditions known to one skilled in the art, particularly acid hydrolysis carried out with an acid such as hydrochloric acid and benzene sulfonic acid or p-toluene sulfonic acid, formic acid or trifluroroacetic acid. The phthalimido group is eliminated by hydrazine. A list of the various protector groups which can be used will be found for example in French patent No. 2,499,995.

The products described above can, if desired, be subjected to salification reactions by a mineral or organic acid according to the usual methods known to one skilled in the art. The products described above can optionally be subjected on the optional carboxy functions to salification reactions by a mineral or organic base or to an esterification reaction. These esterification and salification reactions can be carried out according to the usual methods known to one skilled in the art.

The optional esterified carboxy functions of the products can be optionally reduced into an alcohol function by methods known to one skilled in the art and particularly by lithium aluminum hydride in a solvent such as tetrahydrofuran or dioxane or ethyl ether.

The optional conversions of the ester functions into an acid function of the products can be optionally carried out under the usual conditions known to one skilled in the art, particularly by acid or alkaline hydrolysis for example with sodium hydroxide or potassium hydroxide in an alcoholic medium such as in methanol or also with hydrochloric acid or sulfuric acid.

The optional cyano functions of the products can be optionally converted into an acid function under the usual conditions known to one skilled in the art, for example by hydrolysis carried out in an acid medium such as in sulfuric acid, glacial acetic acid and water mixture, these three compounds being preferably in equal proportions, or also in a mixture of sodium hydroxide, ethanol and water at reflux.

The optional alkoxy functions such as methoxy of the products described above can be optionally converted into an alcohol function under the usual conditions known to one skilled in the art, for example with boron tribromide in a solvent such as methylene chloride, with pyridine hydrobromide or hydrochloride or also with hydrobromic acid in water or acetic acid at reflux.

The oxidation of the optional sulfur into the sulfoxide or sulfone can be carried out using a peracid, for example, metachloroperbenzoic acid. The conversion of the ketone function into an oxime function can be carried out by the action of an amino compound, for example hydroxylamine hydrochloride in the presence of a weak base such as sodium acetate. The conversion of the ketone function into an alcohol can be carried out using an organometallic compound, for example an organozinc compound or an organomagnesium compound.

The conversion of the amine function into an amide can be carried out using an isocyanate, for example propylisocyanate. The optional substitution reactions by halogen and particularly the substitution reactions of the hydroxyl or mercapto function by halogen can be optionally carried out under the usual conditions known to one skilled in the art such as with thionyl chloride, phosphorus pentachloride ($PCl_5$) or phosphorus oxychloride ($POCl_3$) in a solvent such as ether, methylene Chloride or tetrahydrofuran in the optional presence of a base such as pyridine, or with a methane tetrahalide such as methane tetrachloride or tetrabromide and triphenylphosphine.

The optional optically-active forms of the products of formula I can be prepared by resolution of the racemics according to the usual methods.

The novel compositions of the invention for inhibiting the effects of angiotensin II are comprised of an effective amount of at least one compound of formula I and its salts sufficient to inhibit angiotensin II effects and an inert pharmaceutical carrier. The compositions may be in the forms of tablets, dragees, capsules, granules, suppositories, ointments, creams, gels, aerosol preparations and injectable solutions or suspensions.

Examples of the inert carriers or excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions are endowed with antagonistic properties for the angiotensin II receptor and are thus in particular inhibitors of the effects of angiotensin II, especially of the vasoconstrictive effect and also of the trophic effect at the level of the myocytes. They can be used in the treatment of arterial hypertension, cardiac insufficiencies, renal insufficiencies and in the prevention of the post-angioplastic recurrence of stenosis and in particular in cerebral vascular injuries. They can also be used in the treatment of certain gastro-intestinal, gynecological disorders and in particular for a relaxing effect at the level of the uterus.

The novel method of the invention for inhibiting angiotensin II effects in warm-blooded animals including humans comprises administering to warm-blooded animals an amount of at least one compound of formula I and its salts sufficient to inhibit angiotensin II effects. The compounds may be administered orally, rectally, parenterally or topically to the skin and mucous membranes. The usual daily dosage is 0.015 to 1.5 mg/kg depending on the condition treated, the specific compound and the method of administration.

The starting compound of formula II may be prepared by reacting a compound of the formula

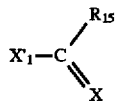
IIa wherein X is oxygen or NH, $R_{15}$ is hydroxyl, alkoxy, amino or halogen and $X'_1$ has the meaning indicated above with a compound of the formula

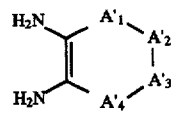
IIb wherein $A'_1$, $A'_2$, $A'_3$ and $A'_4$ have the above meanings to obtain the compound of the formula II.

The present invention also relates preferably to a process for the preparation of a product of formula II comprising reacting a compound of the formula

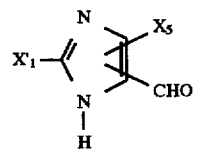
Fa wherein $X_5$ is selected from the group consisting of alkyl, alkoxy, hydroxyl, formyl, alkylthio, phenylthio, benzylthio, free, salified or esterified carboxy or amino optionally substituted by one or two alkyl such that the alkyl and phenyl are optionally substituted by at least one member of the group consisting of halogen, hydroxyl, alkyl, aralkoxy, and in which the reactive functions are if necessary protected.

With a lithium or magnesium halide of the formula

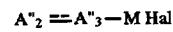
Fb wherein Hal is halogen, M is lithium or magnesium and

is either ethenyl optionally substituted by 1, 2 or 3 $R'_1$ and $R'_2$ as defined above, in which the optional reactive functions are optionally protected, or one of $A''_2$ and $A''_3$ is amino optionally substituted by 1 or 2 $R'_1$ and $R'_2$ as defined above, for $R_1$ and $R_2$ respectively in which the optional reaction functions are optionally protected by protective groups, in which the optional reactive functions are optionally protected as above to obtain a product of the formula

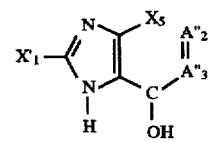
Fc wherein $X'_1$, $X_5$, $A''_2$ and $A''_3$ have the above meanings, which is oxidized to obtain a compound of the formula

Fd wherein $X'_1$, $X_5$, $A''_2$ and $A''_3$ have the above meanings which is subjected to a cyclization reaction to obtain a product of the formula

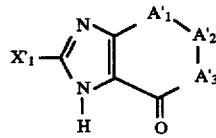
Fe wherein $X'_1$, $A'_1$, $A'_2$ and $A'_3$ have the above meanings which products of formula Fe may be a product of formula II which, if appropriate, is converted to obtain another product of formula II or which product of formula Fe is converted into a product of formula II by subjecting it, if desired and if necessary, to one or more of the following reactions in any order:

an elimination reaction of the protector groups that can be carried by the protected reactive functions, a salification reaction by a mineral or organic acid or by a mineral or organic base to obtain the corresponding salt, an esterification reaction of the acid function, a saponification of the ester function into an acid function, a conversion reaction of the alkoxy function into hydroxyl function, a conversion reaction of cyano function into an acid function, a conversion reaction of the ketone function into a cyano function, a reduction reaction of the carboxy function into an alcohol function, a resolution reaction of the racemic forms, the said products of formula II thus obtained being in all the possible racemic, enantiomeric and diastereoisomeric isomer forms.

It can be noted that when $X_5$ is formyl, alkylthio, phenylthio or benzylthio, these groups being, if necessary, protected, the starting products of formula II as defined above can be prepared in which $A'_1$ and $A'_2$ different from each other, are selected from sulfur, —CH$_2$— or amino, all optionally substituted by alkyl, phenyl or benzyl being themselves substituted as indicated above, and when $X_5$ is hydroxyl or alkoxy, these groups being, if necessary, protected, the starting products of formula II as defined above can be prepared in which $A'_1$ is oxygen.

Such preparations are illustrated in the examples thereafter.

The compounds of formula II can particularly be a compound of the formula

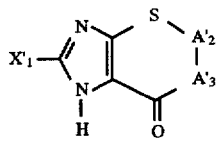

V or also a compound of the formula

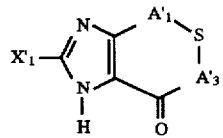

VI

The diagrams 1, 2, 3 and 4 hereafter give examples of the preparation of such compounds of formulae V and VI. In the following diagrams,

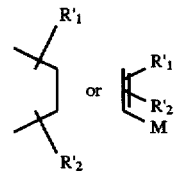

mean that the hydrocarbyl group can be if appropriate unsubstituted or substituted on each of the 2 carbons by 1 or 2 $R'_1$ and $R'_2$

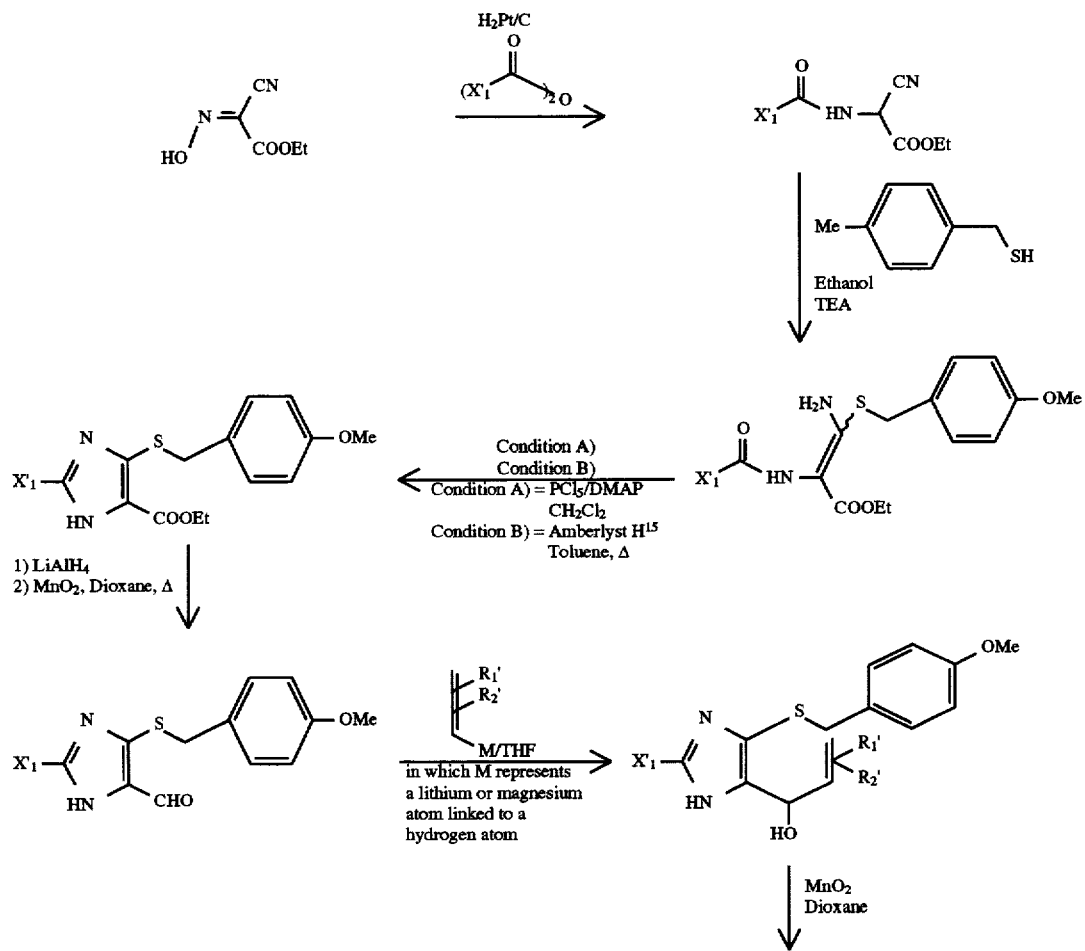

Diagram 1

-continued
Diagram 1
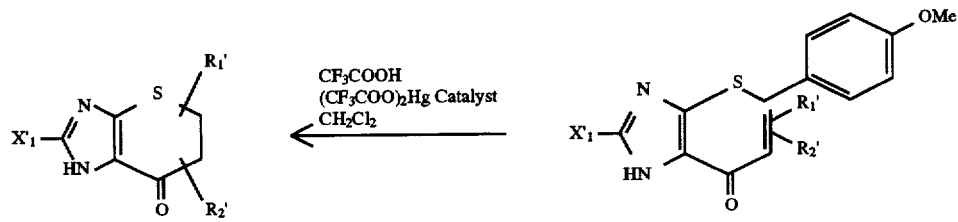
Diagram 2
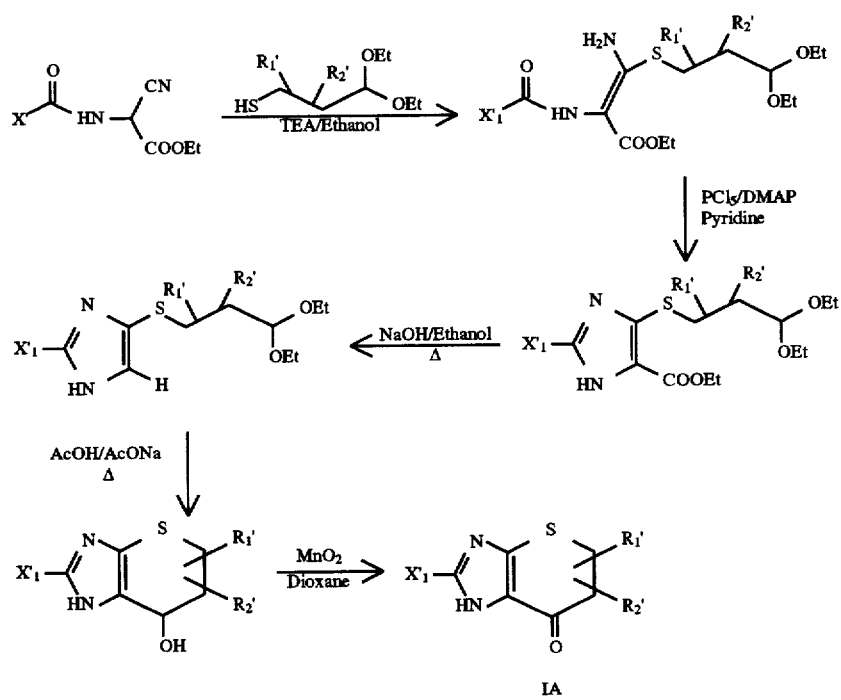
Diagram 3
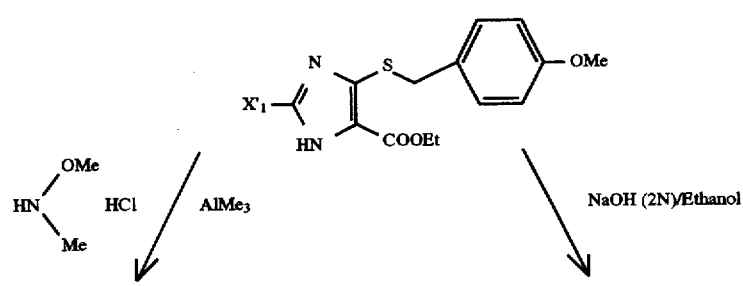

-continued
Diagram 3
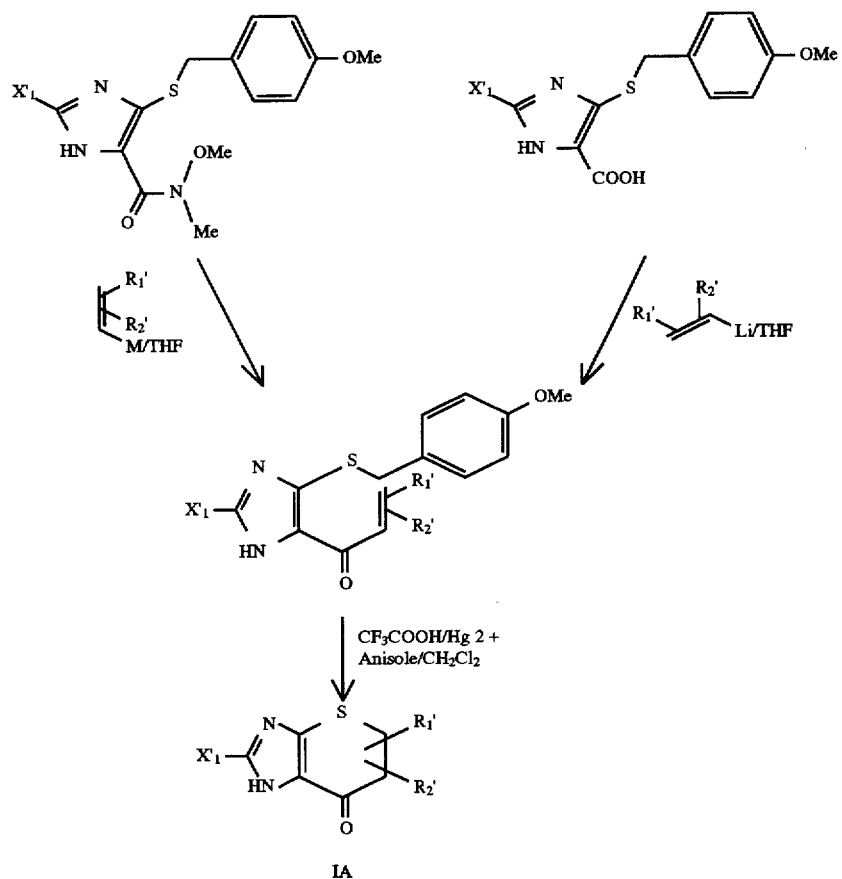
Diagram 4
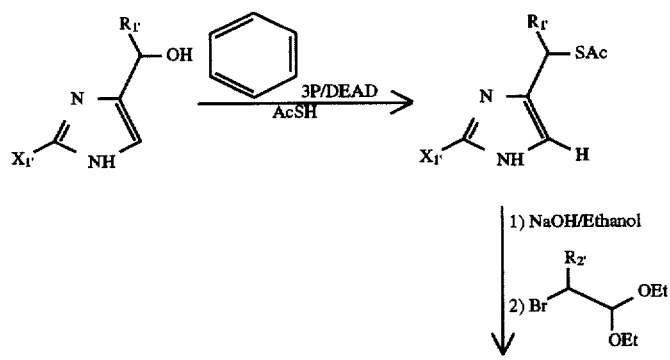

-continued
Diagram 4

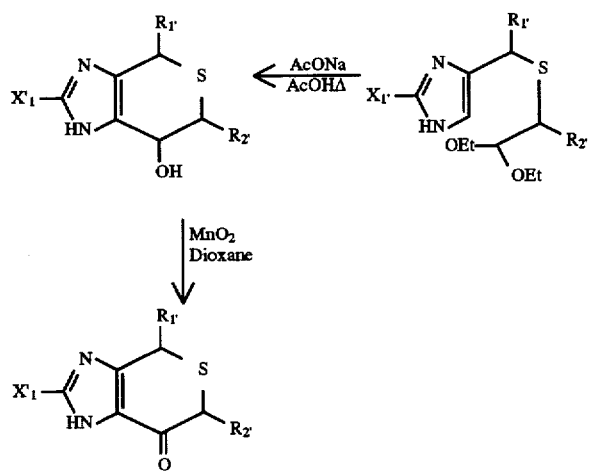

DAMP is dimethylaminopyridine, TEA is triethylamine, DEAD is diethylazodicarboxylate and DME is dimethylethane in the previous diagrams.

A process for the preparation of certain products of formula III comprising subjecting a compound of the formula

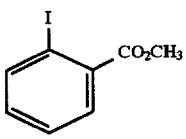    IIIa which is methyl iodobenzoate which can be found in the form of a product marketed by JANSSEN to the action of a compound of the formula

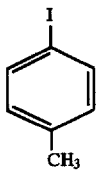    IIIb which is iodotoluene which can be found in the form of a product marketed by FLUKA, the reaction being carried out in the presence of powdered copper at a temperature of approximately 100° C. to 300° C. to obtain a product of the formula

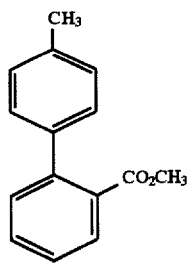    IIIc of which the esterified carboxy can optionally be released from the alkyl by standard methods known to one skilled in the art or indicated above, for example by acid or alkaline hydrolysis, the esterified carboxy or the free carboxy obtained after release of the alkyl being able to be subjected to reduction, addition or substitution reactions in any order, these reactions being able to be carried out by the standard methods known to one skilled in the art, which product of formula IIIc can be subjected to a bromination reaction on the methyl by standard methods known to one skilled in the art, for example by the action of n-bromosuccinimide in carbon tetrachloride, then to an addition reaction of the amine function under the conditions indicated in Ragnarsson et al. Acc. Chem. Res. 1991, Vol. 24, pp. 285–289 and cited ref. to obtain from the product of formula IIIc compounds of formula III as defined above.

By operating in the same manner as described previously, starting with products of formulae:

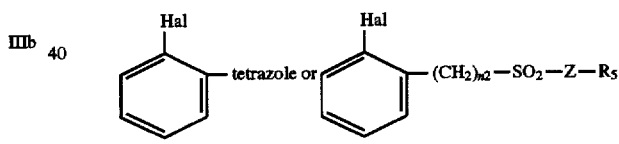

wherein Hal is halogen which can be bromine or preferably iodine, other compounds of formula III are thus obtained.

Examples of the preparation of compounds of formula III are described in the literature and examples are given in U.S. Pat. No. 4,880,804 and in European Patent Applications No. 0,400,974 and No. 0,461,040.

The starting compounds of formulae IIa, IIb, IIIa and IIIb may be available commercially or can be prepared by the usual methods known to one skilled in the art.

The products of formula Fa used at the start of the process are known products or can be prepared from the corresponding alcohol or ester by operating conditions known to one skilled in the art.

Finally, an object of the present invention is as intermediate products, the compounds of formulae II and III.

In addition to the products described in the examples, the following products are products which can be obtained within the scope of the invention. In the products below, Ar is

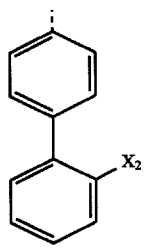
wherein $X_2$ has the above meaning and is preferably cyano, free salified or esterified carboxy, optionally substituted or salified tetrazolyl or $-(CH_2)_{n2}-SO_2-Z-R_5$ as defined above representing particularly
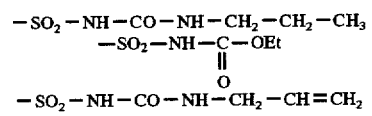
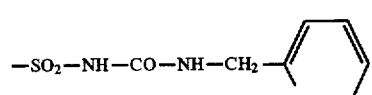
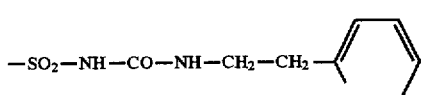
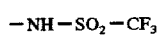
In the products hereafter, S can be replaced by O or NH or $NR_1$ with $R_1$ as defined above and n is 0, 1 or 2.
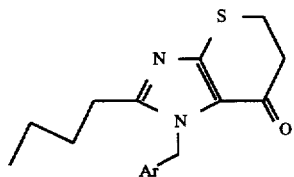
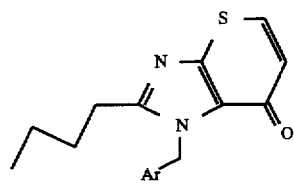
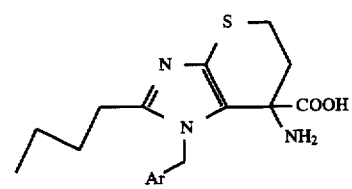
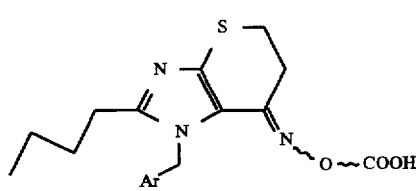
-continued
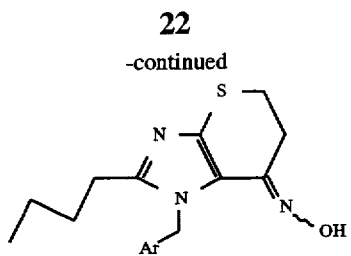
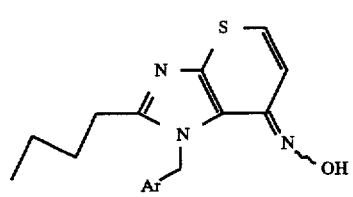
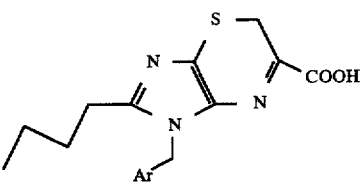
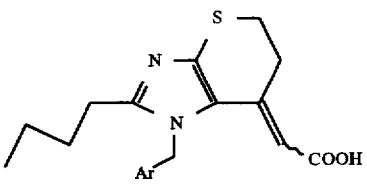
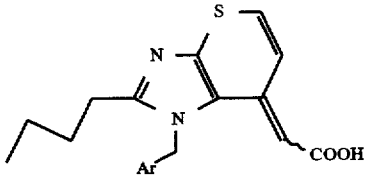
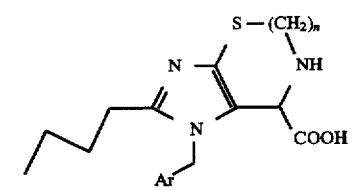
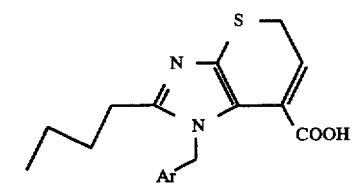
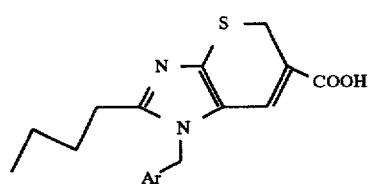

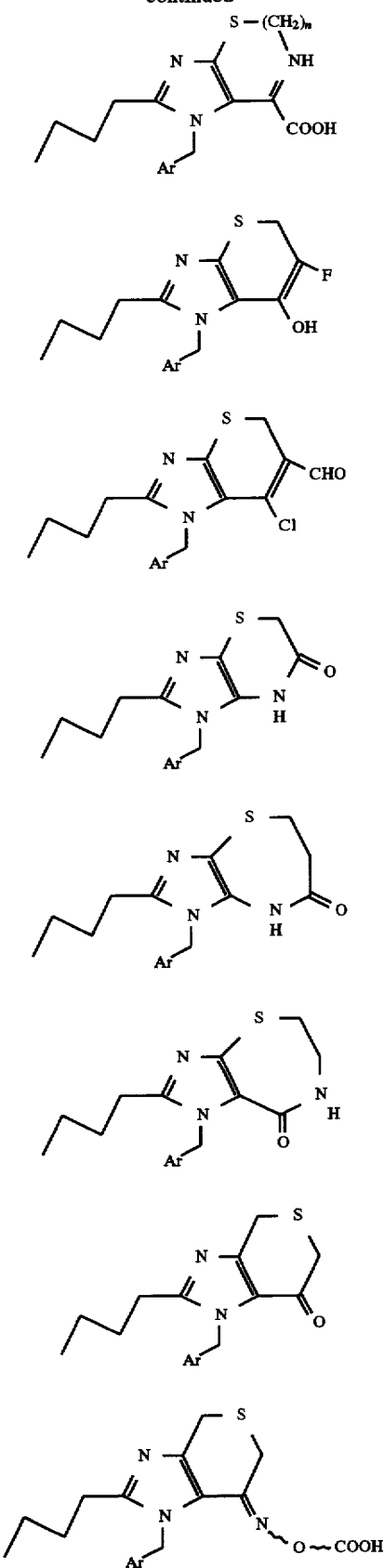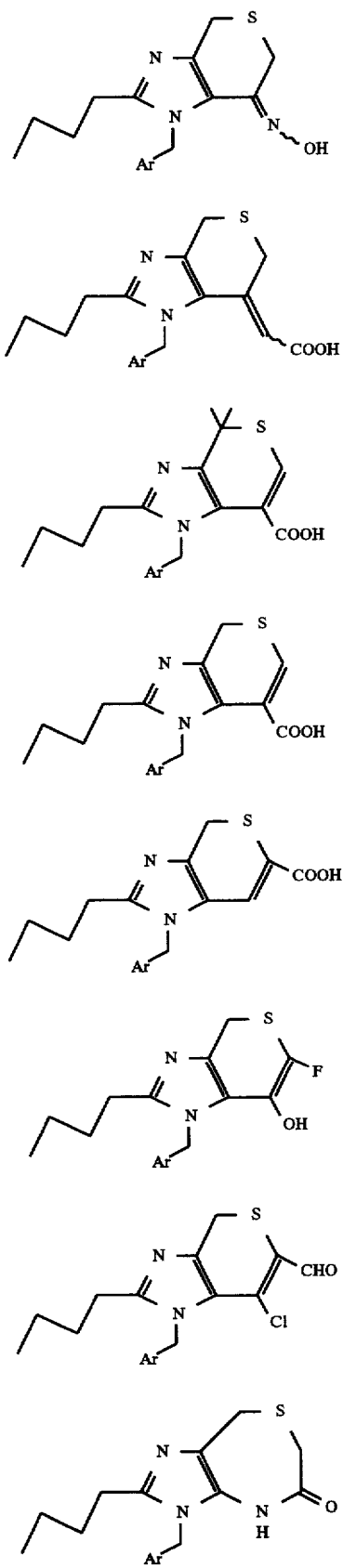

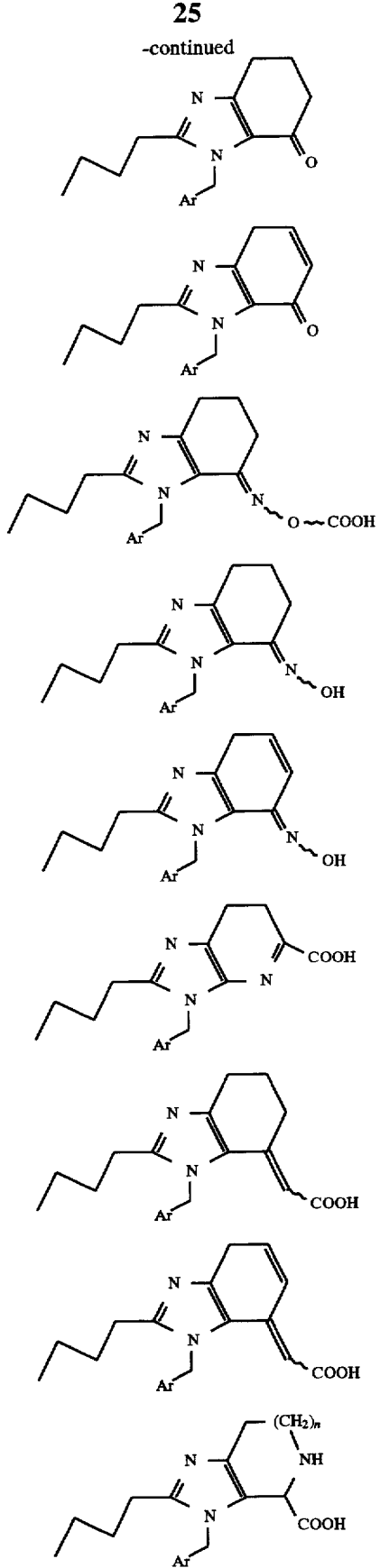
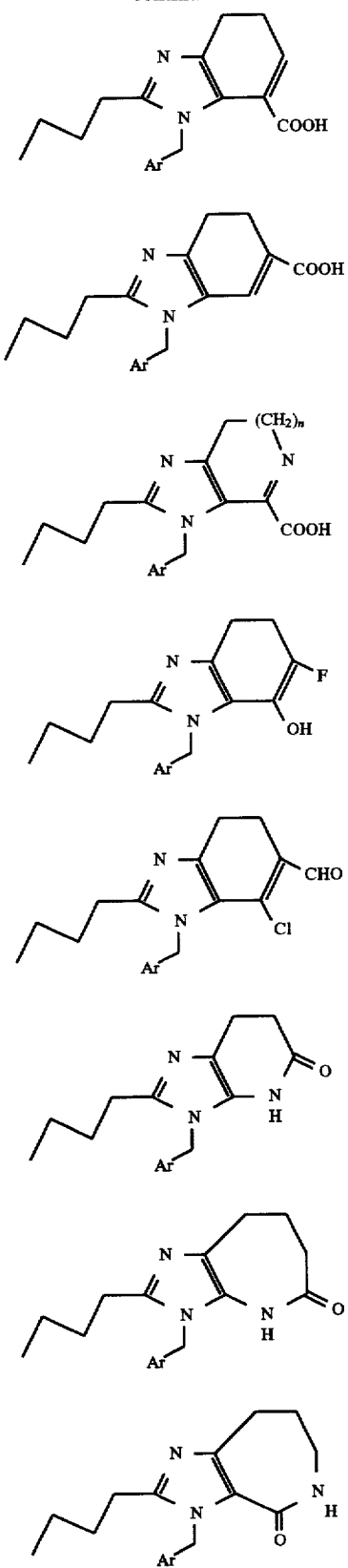

Other preferred molecules can also be mentioned:

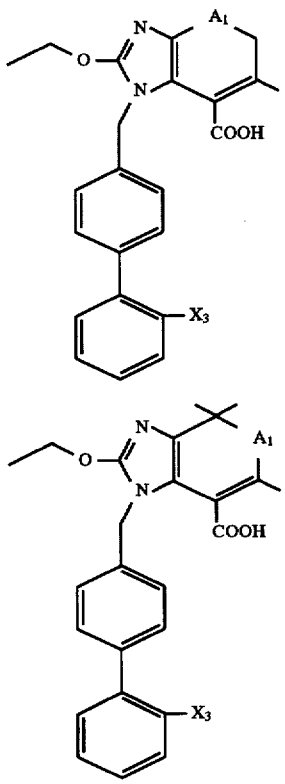

in which $A_1$ and $A_2$ are sulfur or oxygen and $X_3$ is:

or $NH-SO_2-CF_3$.

In the following examples, there are described several preferred embodiments to illustrate invention. However, it is to be understood that the invention is not intended to be limited to the specific embodiments.

EXAMPLE 1

4'-[(2-butyl-6,7-dihydro-7-oxo-thiopyrano-(2,3-d)imidazol-1(5H)-yl)-methyl]-N-[dimethylamino)-methylene]-1(1,1'-biphenyl)-2-sulfonamide

Stage 1

2-butyl-5-[4-methoxy-benzyl-thio]-1H-imidazole-4-methanol 50 g or 143.5 mmol of ethyl 2-butyl-4-[4-methoxy-benzyl-thio]-1H-imidazole-5-carboxylate[prepared as indicated in the European Patent Application No. 0,465,368] were solubilized in 300 ml of methylene chloride and the mixture was cooled to −78° C. With stirring, 68.3 g (480 mmol) and 2N DIBAH in 400 ml of toluene were added and then the medium was allowed to return to ambient temperature for about 30 minutes. The reaction medium was hydrolyzed with 130 ml of water, filtered, washed with 500 ml of methylene chloride and then 3 times with 500 ml of a methylene chloride/methanol solution (9-1). After evaporation to dryness, 100 g (orange solid) were recovered and 500 ml of methylene chloride/methanol (9-2) were added. The insoluble white product was filtered off and the organic phase was evaporated to dryness to obtain 46.55 g of product (orange-yellow powder) which was purified on a silica column with methanol/methylene chloride (5-95) as eluant to obtain 32.49 g of the expected product.

ANALYSES

IR, cm$^{-1}$, nujol absence of C=O absorption NH/OH region heterocycle+aromatic: 1610, 1580, 1510 cm$^{-1}$

Stage 2

2-butyl-5-[4-methoxy-benzyl-thio]-1H-imidazole-4-carboxylaldehyde 32.51 g or 106mmol of the product of Stage 1 were solubilized in 250 ml of dioxane and 46.1 g (530.5 mmol) of powdered $MnO_2$ were added with stirring. The reaction medium was heated to 50° C. with stirring and after about 7 hours of heating at 50° C., 18.44 g of $MnO_2$ were added and the mixture was held at 50° C. The reaction medium was allowed to cool overnight to ambient temperature. 750 ml of ethyl acetate were added with stirring then filtration and taking to dryness to obtain 33.45 g (pink powder) which was purified on silica (eluant: ethyl acetate/flugene (1-1)) to obtain 28.77 g of the expected product.

ANALYSES

IR, cm$^{-1}$, CHCl$_3$ =NH: 3424, 3221 cm$^{-1}$ C=O: complex approx. 1640 cm$^{-1}$ heterocycle+aromatic: 1611, 1585, 1540, 1513, 1497 cm$^{-1}$

Stage 3

2-butyl-α-ethenyl-5-[4-methoxy-benzyl-thio]-1H-imidazole-4-methanol 28.77 g or 94.5 mmol of the product of Stage 2 were solubilized in 180 ml of THF (tetrahydrofuran) and the mixture was taken to −78° C. 37.22 g or 283.5 mmol of vinyl magnesium bromide were introduced with stirring and the reaction mixture was stirred for about one hour at a temperature of about −10° C. The reaction medium was hydrolyzed at about −10° C. and then 150 ml of methanol were added. 500 ml of an ice-cooled aqueous solution saturated with ammonium chloride were then added and extraction was carried out 3 times with 250 ml of a mixture of methanol/methylene chloride (1-9). The combined organic phases were washed with 300 ml of water, then dried. After filtration and evaporation, 41.94 g (orange-yellow powder) were obtained and the powder was solubilized hot, then at ambient temperature in ethyl acetate. Filtration was carried out, followed by rinsing with ethyl acetate, then with ether and drying to obtain 24.11 g (white powder) of the expected product.

ANALYSES

IR, cm$^{-1}$, CHCl$_3$ Absence of C=O Complex OH 3600–3550 cm$^{-1}$ =C—NH 3440 cm$^{-1}$ Aromatic and heteroaromatic C=C: 1640, 1610, 1583, 1510 cm$^{-1}$, with possible —CH=CH$_2$ at 930 cm$^{-1}$.

Stage 4

1-[2-butyl-4-[4-methoxy-benzyl-thio]-5-imidazolyl]-2-propen-1-one 3 g of the product of Stage 3 were dissolved at 30° C. in 60 ml of dioxane and the medium was allowed to return to ambient temperature. 1.56 g (2 equivalents) of $MnO_2$ were added about every 30 minutes for about 2 hours, that being 10 equivalents in total. The mixture was poured into 500 ml of ethyl acetate and filtration was carried out. The filtrate was evaporated to dryness to obtain 2.7 g of a yellow solid which was chromatographed on silica with AcOEt/flugene (1-2) to obtain 2.1 g of the expected product (vivid yellow solid).

ANALYSES

IR CHCl$_3$ NH 3425, 3220 cm$^{-1}$ carbonyl 1635 cm$^{-1}$ heterocycle, aromatic C=C 1610, 1585, 1533, 1513, 1487 cm$^{-1}$ Stage 2-butyl-5,6-dihydro-thiopyrano[2,3-d]-imidazol-7(1H)-one 2.1 g of the product of Stage 4 (6.4 mmoles) were dissolved in 65 ml of dichloromethane (10 ml/mmole) and the following were introduced at about 0° C.:

25 ml of anisole (4 ml/mmole)

12.5 ml of trifluoroacetic acid (2 ml/mmole) and 271 mg of mercuric trifluoroacetate (10% molar). The reaction mixture was allowed to return to about 20° C. and was stirred for about 5 hours and then evaporated to dryness at about 45° C. 50 ml of a saturated solution of NaCHO$_3$ were added to reach a pH of 8–9 and 100 ml of water were added. Extraction was carried out with CH$_2$Cl$_2$ (3 times) and the extracts were dried to obtain 3.19 g of a yellow solid which was impasted in cyclohexane to obtain 1.376 g of the expected product (clear yellow powder).

ANALYSES

IR, CHCl$_3$ =C—NH 3430, 3196 cm$^{-1}$ carbonyl 1637 cm$^{-1}$ C=C, C=N 1533, 1497 cm$^{-1}$ Stage 6

4'-[(2-6,7-dihydro-7-oxo-thiopyrano-(2,3-d)-imidazol-1 (5H)-yl)-methyl]-N-[(dimethylamino)-methylene]-(1,1'-biphenyl)-sulfonamide 882.8 mg (1 equivalent) of the product of Stage 5 were dissolved in 60 ml of dimethylformamide and 764 mg (1.3 equivalents) of potassium carbonate were introduced. The reaction medium was stirred for about 5 minutes and 2.08 g of 4'-(bromo-methyl)-N-[(dimethylamino)-methylene]-(1,1'-biphenyl)-2-sulfonamide dissolved in 70 ml of DMF were added. The mixture was stirred for about 21 hours and then evaporated to dryness and extracted with (water/AcOEt) 3 times. The organic phase was evaporated to dryness to obtain 2.77 g of a yellow powder which was chromatographed on silica in ethyl acetate to obtain 1.91 g of the expected product (white/yellow solid).

ANALYSES

IR CHCl$_3$ 1628 cm$^{-1}$, strong absorption: ketone+—SO$_2$—N=C—N SO$_2$: 1347, 1150 cm$^{-1}$

EXAMPLE 2

4'-[(2-butyl-6,7-dihydro-7-oxo-thiopyrano-(2,3-d) imidazol-1(5H)-yl)-methyl]-(1,1'-biphenyl)-2-sulfonamide 1.5 g of the product of Example 1, 15 ml (10 volumes) of ethanol, 4.5 ml (3 volumes) of concentrated HCl were mixed together and the mixture was stirred at reflux for about 3 to 4 hours. The medium was made basic with 2N sodium hydroxide to a pH of 8–9 and 200 ml of water were added. Extraction was carried out 3 times with dichloromethane and the organic phase was washed with water, and taken to dryness to obtain 1.06 g of a yellow solid which was purified on silica, eluant AcOEt/cyclohexane (5-5) to obtain 760 mg of the expected product (white/yellow solid).

ANALYSES

IR, CHCl$_3$ SO$_2$NH$_2$ 3450, 3350 cm$^{-1}$ carbonyl 1644 cm$^{-1}$ aromatic, heteroaromatic, NH$_2$ def. 1543, 1520, 1496 cm$^{-1}$.

EXAMPLE 3

4'-[(2-butyl-6,7-dihydro-7-oxo-thiopyrano-(2,3-d) imidazol-1-(5H)-yl)-methyl]-N-[(propylamino)-carbonyl]-(1,1'-biphenyl)-2-sulfonamide 360 mg (1 equivalent) of the product of Example 2 were dissolved in 10 ml of DME (dimethylethane) and 224 mg (2 equivalents) of K$_2$CO$_3$ were added. The mixture was stirred for about one hour at ambient temperature before adding 0.110 ml (1.5 equivalents) of propylisocyanate. The reaction medium was heated at 85° C. for 3 to 4 hours and 5 ml of water were added. Acidification was carried out to a pH of 3 with 2 mol of 1N HCl, followed by extraction 3 times with CH$_2$Cl$_2$. The organic phase was washed with a saturated solution of NaCl and evaporated to dryness to obtain 466.2 mg of a crude white solid which was purified on silica, eluant CH$_2$Cl$_2$/AcOEt (2-1) to obtain 316 mg of the expected product as a white solid.

ANALYSES

IR, CHCl$_3$=C—NH 3371, 3404 cm$^{-1}$ carbonyl 1716, 1640 cm$^{-1}$ aromatic, heteroaromatic, amide 1593, 1540, 1493 cm$^{-1}$ Microanalysis

|  | C | H | N | S |
| --- | --- | --- | --- | --- |
| % calculated: | 59.977 | 5.965 | 10.361 | 11.86 |
| % found: | 59.8 | 6.1 | 10.1 | 11.8 |

EXAMPLE 4 ethyl-2-(4'-((2-butyl-6,7-dihydro-7-oxo-thiopyrano-(2,3-d-imidazol-1-(5H)-yl)-methyl]-(1,1'-biphenyl)-sulfonyl-carbamate 378 mg (1 equivalent) of the product of Example 2 were dissolved in 10 ml of DME and 235.7 Tag (2 equivalents) of K$_2$CO$_3$ were added. The mixture was stirred for about 1 hour and then 0.32 ml (4 equivalents) of ethyl chloroformate were added. The reaction mixture was stirred for about 21 hours at ambient temperature, then for about I hour at 60° C. 10 ml of a saturated solution of NaHCO$_3$ were added to a pH of 6–7, and extraction was carried out 3 times with ethyl acetate. The organic phase was washed with a saturated solution of NaCl and evaporated to dryness to obtain 485 g of a clear yellow solid which was purified on silica (eluant AcOEt-cyclohexane (7-3)) to obtain 295 mg of the expected product (yellow solid).

ANALYSES

IR, CHCl$_3$=C—NH 3385 cm$^{-1}$ carbonyl 1750, 1641 cm$^{-1}$ aromatic, heteroaromatic, amide 1594, 1564, 1514, 1493 cm$^{-1}$ Microanalysis

|  | C | H | N | S |
| --- | --- | --- | --- | --- |
| % calculated: | 59.183 | 5.539 | 7.963 | 12.153 |
| % found: | 59.0 | 5.8 | 7.8 | 11.8 |

EXAMPLE 5

4'-[(2-butyl-7-(hydroxyimino)-1,5,6,7-tetrahydro-thiopyrano[2,3-d)-imidazol-1-yl)-methyl]-(1,1'-biphenyl)-2-sulfonamide 1 g of the product of Example 2 (2.19 mmoles), 20 ml of ethanol, and 5 ml of methanol were mixed together and 0.538 g of sodium acetate (6.57 mmoles) and 0.460 g of hydroxylamine hydrochloride (6.67 mmoles) were introduced all at once. The reaction mixture was refluxed for about 48 hours and after a further 0.304 g of hydroxylamine hydrochloride were added (4.37 mmoles, 2 equivalents), the mixture was stirred for about 48 hours. The precipitate formed was filtered off, washed with water and dried to obtain 0.93 g of the desired product melting at >200° C.
ANALYSES IR Spectrum in Nujol $NH_2+OH$ 3390, 3280 $cm^{-1}$ $SO_2$ 1330, 1160 $cm^{-1}$ aromatic 1655 $cm^{-1}$ C=N 1590, 1560, 1548, 1535, 1502 $cm^{-1}$

EXAMPLE 6

4'-[(2-butyl-7-((((propylamino)-carbonyl-oxy)-imino-1,5,6,7-tetrahydro-thiopyrano[2,3-d)-imidazol-1-yl)-methyl]-N-[(propylamino)-carbonyl]-(1,1'-biphenyl)-2-sulfonamide 0.6 g of the product of Example 5 (1.27 mmoles), 9 ml of dimethoxyethane (15 vol.), 0.444 g of potassium carbonate (3.17 mmoles), and 0.298 ml of propylisocyanate (2.5 equivalents, 3.17 mmoles) were mixed together and the mixture was stirred for about 1 hour. A further 0.06 ml of propylisocyanate were added and the reaction medium stood for about half an hour and then was poured into 20 ml of water and 10 ml of a saturated solution of ammonium chloride. Extraction was carried out 3 times with 20 ml of methylene chloride and the extracts were dried, filtered and dried again to obtain 0.88 g of product which was deposited in solution in one volume of ethyl acetate eluant, on silica. After eluting and drying, 0.325 g of expected product were obtained as a white powder.

EXAMPLE 7

4'-[(2-butyl-7-(hydroxyimino)-1,5,6,7-tetrahydro-thiopyrano[2,3-d)-imidazol-1-yl)-methyl]-N-[(propylamino)-carbonyl]-(1,1'-biphenyl)-2-sulfonamide 283 mg of the product of Example 6 (0.44 mmole), 3 ml of ethanol (10 vol.), and 0.44 ml of 2N sodium hydroxide were mixed together and the mixture was stirred under a current of nitrogen at ambient temperature for about 3 hours. The mixture was heated at about 50° C. for about one hour and after drying, the oily residue was taken up in 5 ml of distilled water. Then, 0.44 ml of 2N hydrochloric acid (2 equivalents) were added and the medium was stirred for about 30 minutes, then filtered, washed with distilled water, and dried to obtain 220 mg of the expected product as a white powder melting at 178° C.
Microanalysis

|  | C | H | N | S |
|---|---|---|---|---|
| % calculated: | 58.35 | 5.98 | 12.60 | 11.53 |
| % found: | 58.0 | 6.0 | 12.2 | 11.3 |

EXAMPLE 8

4'-[(2-butyl-6,7-dihydro-4-oxide-7-oxo-thio-pyrano[2,3-d)-imidazol-1-(5H)-yl)-methyl]-N-[(dimethylamino)-methylene)-(1,1'-biphenyl)-2-sulfonamide 690 mg of the product of Example 1 (1.35 mmoles) and 6.9 ml of methylene chloride were mixed together and a solution of metachloroperbenzoic acid and 326 mg of acid at 70% (1.32 mmoles, 1 equivalent) in solution in 1.6 ml of methylene chloride were introduced at 0° C. The reaction medium was stirred for 4 hours and then allowed to return to ambient temperature. The mixture was poured into 30 ml of water and 5 ml of a saturated sodium bicarbonate solution. Extraction was carried out 3 times with 50 ml of methylene chloride and the extracts were filtered and dried to obtain 950 mg of crude product which was purified by chromatography. The 950 mg of crude product was deposited in solution in one volume of methylene chloride methanol eluant (9703) on a silica column. After eluting, the fraction containing the expected product was isolated and dried to obtain 570 mg of the desired product as a white powder.
ANALYSES IR Spectrum, $CHCl_3$>=O 1676, 1628 $cm^{-1}$ aromatic, heteroatom 1516 $cm^{-1}$ >S→O 1042 $cm^{-1}$.

EXAMPLE 9

4'-[(2-butyl-7-oxo-thiopyrano-[2,3-d]-imidazol-1-(7H)-yl)-methyl]-N-[(dimethylamino)-methylene)-(1,1'-biphenyl)-2-sulfonamide 500 mg of the product of Example 8 (0.949 mmole), 5 ml of $CH_2Cl_2$, 1.5 ml of acetic acid anhydride (3 vol.), and 0.15 ml of methane sulfonic acid (0.3 vol) were mixed together and the mixture was stirred at about 40° C. for 15 hours and was poured into 20 ml of water. The pH was brought to about 6 by the addition of a saturated solution of sodium bicarbonate. Extraction was carried out 3 times with 50 ml of $CH_2Cl_2$ and the extracts were filtered and dried to obtain 500 mg of crude product which was purified by chromatography. The 500 mg of crude product were deposited on a silica column in a $CH_2Cl_2$/MeOH eluant (95-5) and after eluting, the fraction containing the expected product was isolated and dried to obtain 394 mg of the expected product.
ANALYSES IR Spectrum, $CHCl_3$>C=O, C=C, C=N 1628, 1606 $cm^{-1}$ Conjugated system+aromatic 1515 $cm^{-1}$.

EXAMPLE 10

4'-[(2-butyl-7-oxo-thiopyrano-[2,3-d]-imidazol-1-(7H)-yl)-methyl]-(1,1'-biphenyl)-2-sulfonamide 390 mg of the product of Example 9 (0.77 mmole), 4 ml of ethanol (10 vol.), and 1.2 ml of concentrated hydrochloric acid (3 vol) were mixed together and the mixture was refluxed for about 2 hours. After evaporating to dryness, the residue was taken up in 10 ml of water, and a basic pH was obtained by the addition of 4 to 5 ml of concentrated sodium hydroxide. Extraction was carried out 3 times with 50 ml of ethyl acetate, followed by filtration and drying to obtain 320 mg of crude product which was purified by chromatography. 320 mg of crude product were deposited in solution in 1 volume of $CH_2Cl_2$/AeOEt eluant (50-50) on a silica column. After eluting, the fraction containing the expected product was isolated and dried to obtain 260 mg of the expected product as a white powder.
ANALYSES IR Spectrum, $CHCl_3$ OH/NH region 3320, 3215 $cm^{-1}$+ general absorption >C=O 1609 $cm^{-1}$ C=C, aromatic, $NH_2$ def. 1563, 1519, 1504 $cm^{-1}$.

EXAMPLE 11

4'-[(2-butyl-7-oxo-thiopyrano-[2,3-d]-imidazol-1-(7H)-yl)-methyl]-N-((propylamino)-carbonyl)-(1,1'-biphenyl)-2-sulfonamide 250 mg of product A of Example 10, 375 ml of dimethoxy ethane (15 vol.), then 92 mg of potassium carbonate (1.2 equivalents, 0.65 mmoles) were mixed together and then 0.072 ml of propylisocyanate (1.4 equivalents, 0.77 mmoles) were added. The mixture was taken to about 80° C. for about 2 hours and was poured into 30 ml of water and 10 ml of a saturated solution of ammonium chloride. Extraction was carried out 3 times with 50 ml of methylene chloride, followed by filtration and drying to obtain 300 mg of crude product which was purified by chromatography. 300 mg of crude product were deposited in solution in a $CH_2Cl_2$/ AcOEt eluant (50-50) on a silica column. After eluting, the fraction containing the expected product was isolated and dried to obtain 285 mg of product which was subjected to a second purification to obtain 285 mg of the product, 2.8 ml of demineralized water (10 vol.), and 0.529 ml of 2N sodium hydroxide were mixed together. The expected product was precipitated by the addition of 0.529 ml of 2N HCl and after standing for about half and hour, and filtration, the product was washed with demineralized water and dried to obtain 245 mg of the expected product melting at 162° C.

IR Spectrum, $CHCl_3$

NH 3400 (sh) 3369 cm$^{-1}$ max. >C=O 1714, 1601 cm$^{-1}$ Conjugated system, aromatic, amide 1565, 1542, 1501 cm$^{-1}$.

Microanalysis $C_{27}H_{30}N_4O_4S_2$, molecular weight=538.9

|  | C | H | N | S |
|---|---|---|---|---|
| % calculated: | 60.2 | 5.6 | 10.4 | 11.9 |
| % found: | 59.9 | 5.5 | 10.5 | 11.8 |

EXAMPLE 12

4'-[(2-butyl-6,7-dihydro-6-fluoro-7-oxo-thio-pyrano-[2,3-d)-imidazol-1-(5H)-yl)-methyl]-N-((dimethylamino)-methylene)-(1,1'-biphenyl)-2-sulfonamide

Stage A 2-butyl-5,6-dihydro-1-[(2-trimethylsilyl)-ethoxy)-methyl)-thiopyrano-(2,3-d)-imidazol-7(1H)-one 0.99 ml of diisopropylethylamine were added at ambient temperature to 1 g of the product of stage 5 of Example 1 in 10 ml of dichloromethane and the mixture was cooled to 0° C. 1 ml of 2-(trimethylsilyl)-ethoxymethyl chloride was added, and the reaction medium was allowed to return to ambient temperature and was stirred for 2 hours. It was poured into water and extraction was carried out with dichloromethane. The extracts were dried and the solvent was eliminated under reduced pressure. After chromatographing the residue on silica (eluant $CH_2Cl_2$-AcOEt 95-5), 1 g of the expected product was obtained.

IR Spectrum, $CHCl_3$ absence of=C—NH— carbonyl: 1643 cm$^{-1}$ silyl: 840 cm$^{-1}$.

Stage B 2-butyl-5,6-dihydro-6-fluoro-1-[(2-(trimethylsilyl)-ethoxy)-methyl)-thiopyrano-(2,3-d)-imidazol-7(1H)-one 1.76 g of the product of Stage A in 8.75 ml of tetrahydrofuran was cooled to −70° C. and then 5.68 ml of lithium his trimethylsilylamine in a molar solution in tetrahydrofuran were added. The mixture was stirred for 15 minutes at −70° C. and after 1.05 ml of trimethylsilyl trifluoromethane sulfonate was added, the mixture was stirred for 30 minutes at −70° C. 2.5 ml of acetonitrile and then 2.1 g of 1-chloromethyl-4-fluoro-1,4-diazonia-bicyclo-(2,2,2)-octane bis tetrafluoroborate were added. The reaction mixture was stirred at −70° C. for 15 minutes, then was allowed to return to 0° C. with stirring under an inert gas atmosphere. The mixture was poured into ice-cooled water and 20 ml of a saturated aqueous solution of ammonium chloride were added. Extraction was carried out with ethyl acetate and the extracts were dried. The solvent was eliminated under reduced pressure and the residue was chromatographed on silica (eluant: $CH_2Cl_2$-AcOEt 95-5) to obtain 305 mg of the expected product with a $R_f$=0.3 ($CH_2Cl_2$-AcOEt 95-5).

Stage C 2-butyl-5,6-dihydro-6-fluoro-thiopyrano-(2,3-d)-imidazol-7(1H)-one 305 mg of the product of Stage B and 1.75 ml of trifluoroacetic acid were heated at 40° C. for 12 hours in 6.1 ml of dichloromethane. The mixture was poured into water, sodium bicarbonate was added until a pH of 6-7 was obtained. Extraction was carried out with methylene chloride and the solvent was eliminated under reduced pressure to obtain 180 mg of the expected product.

ANALYSES

C=O 1654 cm$^{-1}$ C=C 1537 cm$^{-1}$ C=N 1502 cm$^{-1}$.

Stage D

4'-[(2-butyl-6,7-dihydro-6-fluoro-7-oxo-thiopyrano-[2,3-d]-imidazol-1-(5H}-yl)-methyl]-N-((dimethylamino)-methylene)-(1,1'-biphenyl)- 2-sulfonamide Using the procedure of Stage D of Example 1, 170 mg of the product of Stage C in 2.55 ml of dimethylformamide, 125 of potassium carbonate and 425 mg of bromobiphenyl reagent were reacted to obtain after chromatography on silica (eluant: $CH_2Cl_2$-AcOEt 50-50) 275 mg of the expected product.

IR Spectrum, $CHCl_3$ C=O: 1661 cm$^{-1}$ N=CH—N<: 1630 cm$^{-1}$

EXAMPLE 13

4'-[(2-butyl-6,7-dihydro-6-fluoro-7-oxo-thiopyrano-[2,3-d]-imidazol-1-(5H)-yl)-methyl]-(1,1'-biphenyl)-2-sulfonamide Using the procedure of Example 2, 330 mg of the product of Example 12, 3.3 ml of ethanol and i ml of concentrated hydrochloric acid were reacted to obtain 285 mg of the crude product which was used as is in the following example and melted at 208° C.

IR Spectrum, $CHCl_3$ Absence of N—CH—N<=O: 1680, 1671 cm$^{-1}$ aromatic, heteroaromatic, NH$_2$ def.: 1592, 1500 cm$^{-1}$.

EXAMPLE 14

4'-[(2-butyl-6,7-dihydro-6-fluoro-7-oxo-thiopyrano-[2,3-d]-imidazol-1-(5H)-yl)-methyl]-N-((propylamino)-carbonyl)-(1,1'-biphenyl)-2-sulfonamide Using the procedure of Example 3, 275 mg of the product of Example 13, 2.75 ml of dimethoxyethane, 100 mg of potassium carbonate and 0.065 ml of propylisocyanate were reacted to obtain after extraction with ethyl acetate and chromatography on silica (eluant: dichloromethane-ethyl acetate 7-3 then 5-5), 183 mg of the expected product which was taken up in 3 ml of water. 0.28 ml of 2N sodium hydroxide were added and filtration was carried out and drying under reduced pressure at 50° C. to obtain 100 mg of pure product melting at 188° C.

IR Spectrum, $CHCl_3$ =C—NH: 3400, 3371 cm$^{-1}$ C=O: 1716, 1662 cm$^{-1}$ amide II, conj. system: 1540 cm$^{-1}$.

EXAMPLE 15

4'-[(2-butyl-7-chloro-1,5-dihydro-6-formylthiopyrano-[2,3-d]-imidazol-1-yl)-methyl]-N-((dimethylamino)-methylene)-(1,1'-biphenyl)-2-sulfonamide 50 ml of trichlorethylene and 0.61 of dimethylformamide were cooled to 4° C. and 0.37 ml of phosphoryl chloride were added. The mixture was allowed to return to ambient temperature and 1 g of the product of Stage 6 of Example i in solution in 3 ml of dimethyl-formamide was added. The reaction mixture was heated for 3 hours at 95° C.±5° C., allowed to return to ambient temperature, poured into an aqueous solution of sodium acetate and extracted with methylene chloride. The solvent was eliminated under reduced pressure and the residue was chromatographed on silica (eluant: flugene-AcOEt 3-7) to obtain 624 mg of the expected product which was crystallized from ethyl acetate to melt at 160°C.

IR Spectrum $CHCl_3$ C=O: 1648 $cm^{-1}$ N=C—N: 1628 $cm^{-1}$ aromatics: 1592, 1551, 1516, 1487 $cm^{-1}$.

EXAMPLE 16 ethyl 1-[(2'-(aminosulfonyl)-(1, 1'-biphenyl)-4-yl)-methyl]-2-butyl-1,5-dihydro-thiopyrano-[2,3-d]-imidazol-6-carboxylate 100.1 mg of the product of Example 15, 2 ml of ethanol and 0.1 ml of concentrated hydrochloric acid were refluxed for 4 hours 30 minutes and the mixture was cooled to ambient temperature, poured into 20 ml of water, neutralized with 2N sodium hydroxide and extracted with dichloromethane. The extracts were washed with water, dried,the solvent eliminated under reduced pressure and after chromatography on silica (eluant: AcOEt-cyclohexane 5-5), 34 mg of the expected product were obtained.

IR Spectrum, $CHCl_3$ absence of —N=C—N— $(CH_3)_2$ $NH_2$: 3443, 3340 $cm^{-1}$ C=O: 1655 $cm^{-1}$ C=C: 1585 $cm^{-1}$

EXAMPLE 17 methyl 2-butyl-7-chloro-1,5-dihydro-1-[[2,'-[[[(dimethylamino)-methylene]-amino]-sulfonyl]-(1,1,-biphenyl)-4-yl]-methyl]-thiopyrano-[2,3-d]-imidazol-6-carboxylate 285 mg of the product of Example 15, 6 ml of methanol, 900 mg of magnesium oxide, 127 mg of sodium cyanide and 0.05 ml of acetic acid were stirred for 2 hours at ambient temperature and dilution was carried out with 10 ml of ethyl acetate, followed by filtering and washing with ethyl acetate. The solvent was eliminated under reduced pressure and the residue was chromatographed on silica (eluant: flugene-AcOEt 3-7) to obtain 220 mg of the expected product.

IR Spectrum, $CHCl_3$ C=O: 1712 $cm^{-1}$ N=C—N: 1627 $CM^{-1}$ syst. conj.+aromatics: 1554, 1492 $cm^{-1}$.

EXAMPLE 18 methyl 1'-[(2'-(aminosulfonyl)-(1,1'-biphenyl)-4-yl)-methyl)-2-butyl-7-chloro-1,5-dihydro-thiopyrano-[2,3-d]-imidazole-6-carboxylate 194 mg of the product of Example 17, 4 ml of methanol and 0.2 ml of concentrated hydrochloric acid were heated for 7 hours and 30 minutes at reflux. The reaction medium was poured into water, neutralized with 2N sodium hydroxide, extracted with dichloromethane, washed with water and dried. The solvent was eliminated under reduced pressure and after chromatographing on silica (eluant: cyclohexane-AcOEt 6-4), 100 mg of the expected product were obtained.

IR Spectrum, $CHCl_3$ $NH_2$: 3444 $cm^{-1}$ C=O: 1712 $cm^{-1}$ (max). Conj. syst. +aromatics 1600, 1590, 1544, 1517, 1494 $cm^{-1}$. +$NH_2$

EXAMPLE 19 methyl 2-butyl-7-chloro-1,5-dihydro-1-[[2'-[[[(propylamino)-carbonyl]-amino]-sulfonyl]-(1,1'-biphenyl)-4-yl]-methyl]-thiopyrano-[2,3-d]-imidazol-6-carboxylate Using the procedure of Example 3, 91 mg of the product of Example 18 in 0.9 ml of dimethoxyethane, 60 mg of potassium carbonate and 0.022 ml of propylisocyanate were reacted to obtain 84 mg of the expected product.

IR Spectrum, $CHCl_3$=C—NH: 3404 $cm^{-1}$ C=O complex: 1715 $cm^{-1}$ (max). Conj. syst. +amide II 1600, 1590, 1543, 1517, 1494 $cm^{-1}$. +aromatic

EXAMPLE 20

2-butyl-7-chloro-1,5-dihydro-1-[[2'[[[(propylamino)-carbonyl]-amino]-sulfonyl]-(1,1'-biphenyl)-4-yl]-methyl]-thiopyrano-[2,3-d]-imidazol-6-carboxylic acid 79 mg of the product of Example 19, 1.1 ml of ethanol and 0.26 ml of 2N sodium hydroxide were stirred for 24 hours at ambient temperature. The solvents were eliminated under reduced pressure, followed by taking up in 2 ml of water, neutralizing with 2N hydrochloric acid, stirring for 2 hours at ambient temperature, filtering, washing with water and drying under reduced pressure to obtain 69.7 mg of the expected product melting at ≅200° C.

IR Spectrum Nujol C=O:

1718 (sh.), 1688 (sh.), 1669 $cm^{-1}$ (max.) C=C +aromatic 1594, 1556, 1496 $cm^{-1}$+amide II

EXAMPLE 21 ethyl (2-butyl-1-[[2'-[[[(dimethylamino)-methylene]-aminosulfonyl]-(1,1'-biphenyl)-4-yl]-methyl]-7-hydroxy-1,5,6,7-tetrahydrothiopyrano-[2,3-d]-imidazol-7-yl]-acetate 1) Preparation of the organozinc reagent BrZn—$CH_2$—$CO_2Et$.

3.25 g of zinc and 2 ml of tetrahydrofuran were mixed together under an inert atmosphere and 0.2 ml of 1,2-dibromoethane was added. The mixture was refluxed for 5 minutes and 4.4 ml of ethyl bromoacetate dissolved in 40 ml of tetrahydrofuran was added over one hour while maintaining the temperature at 40°–50° C. The mixture was stirred for 30 minutes at ambient temperature and the product was used as is titre 0.4 M/l.

2) Condensation 25 ml of the reagent prepared above in a solution of 1 g of the product of Stage 6 of Example 1 were introduced under an inert atmosphere into 20 ml of tetrahydrofuran. The mixture was stirred for 16 hours at ambient temperature and then was poured into a saturated aqueous solution of ammonium chloride, extracted with ethyl acetate, washed with salt water, dried and the solvent was evaporated off. The residue was chromatographed on silica (eluant: $CH_2Cl_2$-acetone 8-2) to obtain 224 mg of the expected product.

IR Spectrum $CHCl_3$ OH absorption: 3450 $cm^{-1}$ C=O: 1713 $cm^{-1}$

N=CH—N: 1628 $cm^{-1}$

EXAMPLE 22 ethyl (2-butyl-1-[[2'-[[[(dimethylamino)-methylene]-amino]-sulfonyl]-(1,1'-biphenyl)-4-yl]-methyl]-1,5,6,7-tetrahydrothiopyrano-[2,3-d]-imidazol-7-ylidene]-acetate 875 mg of the product of Example 21 and 20 ml of toluene were stirred for 2 hours at reflux in the presence of 14 mg of p-toluene sulfonic acid. The solvent was evaporated off and the residue was chromatographed on silica (eluant: $CH_2Cl_2$-AcOEt 5-5) to obtain 593 mg of the expected product melting at 100° C.

IR Spectrum, $CHCl_3$ Absence of OH C=O: 1700 $cm^{-1}$ (conj. ester) —N=CH—N 1628 $cm^{-1}$ C=C+aromatic: 1504 $cm^{-1}$

EXAMPLE 23 ethyl 1-[[2'-(aminosulfonyl)-(1,1'-biphenyl)-4-yl]-methyl]-2-butyl-1,5,6,7-tetrahydrothiopyrano-[2,3-d]-imidazol-7-ylidene]-acetate 570 mg of the product of Example 22 in 5.7 ml of ethanol and 0.57 ml of 2N hydrochloric acid were stirred for 6 hours at reflux and the reaction mixture was stirred for 16 hours at ambient temperature, poured into water, neutralized with 2N sodium hydroxide, extracted with dichloromethane, washed with water and dried. The solvent was evaporated off and after chromatographing on silica (eluant: $CH_2Cl_2$-AcOEt 8-2), 225 mg of the expected product were obtained.

IR Spectrum $CHCl_3$ Absence of N=CH—N $NH_2$: 3442, 3344 $cm^{-1}$ C=O: 1699 $cm^{-1}$ C=C+aromatic: 1600, 1540, 1503 $cm^{-1}$

EXAMPLE 24 ethyl (2-butyl-1-[[2'-[[[propylamino)-carbonyl]-aminosulfonyl]-(1,1'-biphenyl)-4-yl]-methyl]-1,5,6,7-tetrahydrothiopyrano-[2,3-d]-imidazol-7-ylidene]-acetate Using the procedure of Example 3, 210 mg of the product of Example 23, 2.1 ml of dimethoxyethane, 110 mg of potassium carbonate and 0.056 ml of propylisocyanate were reacted to obtain 147 mg of the expected product melting at 170° C.

IR Spectrum, $CHCl_3$ —C=NH: 3400, 3380 $cm^{-1}$ C=O: 1715, 1654 $cm^{-1}$ Conj. syst. +aromatic 1595, 1540, 1503 $cm^{-1}$+amide II

EXAMPLE 25

2-(2-butyl-1-[[2'-[[[propylamino)-carbonyl]-aminosulfonyl]-(1,1,-biphenyl)-4-yl]-methyl]-1,5,6,7-tetrahydrothiopyrano-[2,3-d]-imidazol-7-ylidene]-acetic acid Using the procedure of Example 20, 135 mg of the product of Example 24, 2.7 ml of ethanol and 0.44 ml of 2N sodium hydroxide were reacted to obtain 112 mg of the expected product melting at 130° C.

IR Spectrum, $CHCl_3$ General absorption NH/OH C=O: 1704, 1695 $cm^{-1}$. Conj. syst. +aromatic 1592, 1542, 1510 $cm^{-1}$+amide II

EXAMPLE 26

[[[1-[[2,-(aminosulfonyl)-(1,1'-biphenyl)-4-yl]-methyl]-2-butyl]-1,5,6,7-tetrahydrothiopyrano-[2,3-d]-imidazol-7-ylidene]-amino]-oxy]-acetic acid 370 mg of the product of Example 2 were mixed with 3.7 ml of ethanol and 3.7 ml of methanol and 400 mg of sodium acetate and 524 mg of carboxymethylamine hemichloride were added. The mixture was heated for 48 hours at reflux and 400 mg of sodium acetate and 520 mg of carboxymethylamine hemichloride were added. Reflux was continued for 24 hours and the reaction medium was allowed to cool, poured into water, acidified by the addition of 2N hydrochloric acid, extracted with ethyl acetate and dried. The solvent was evaporated under reduced pressure and after chromatographing on silica (eluant: $CH_2Cl_2$-MeOH 95-5), 120 mg of the expected product were obtained.

IR Spectrum, Nujol General absorption NH/OH C=O: 1738, 1680 $cm^{-1}$. Conj. syst. +aromatic 1590, 1520 $cm^{-1}$+ $COO^-$

EXAMPLE 27

2-[[[2-butyl-1-[[2'-[[[[propylamino)-carbonyl]-aminosulfonyl]-(1,1'-biphenyl)-4-yl]-methyl]-1,5,6,7-tetrahydrothiopyrano-[2,3-d]-imidazol-7-ylidene]-amino]-oxy]-acetic acid Using the procedure of Example 14, 165 mg of the product of Example 26, 2.4 ml of dimethoxyethane, 95 mg of potassium carbonate and 0.038 ml of propylisocyanate were reacted to obtain after chromatographing on silica (eluant: AcOEt-AcOH 99-1), 108 mg of product which, after purification, 72 mg of expected product were obtained melting at 132°-134° C.

IR Spectrum, Nujol General absorption NH/OH C=O: 1710, 1670 $cm^{-1}$ C=N, aromatic, heterocycle, $COO^-$: 1600, 1545, 1520 $cm^{-1}$

EXAMPLE 28

4'-[[2-butyl-7-hydroxy-7-methyl-1,5,6,7-tetrahydrothiopyrano-]2,3-d]-imidazol-1-yl]-methyl]-N-[(dimethylamino)-methylene]-(1,1'-biphenyl)-Z-sulfonamide Using the procedure of Example 21, 102 mg of the product of Stage 6 of Example 1, 5 ml of tetrahydrofuran and 0.333 ml of 3M solution of methyl magnesium chloride in tetrahydrofuran were reacted to obtain 56 mg of the expected product.

IR Spectrum, $CHCl_3$ Absorption OH+associated: 3590 $cm^{-1}$ N=CH—N: 1627 $cm^{-1}$ aromatic: 1590 $cm^{-1}$ heterocycle: 1540, 1512 $cm^{-1}$

EXAMPLE 29

4'-[[2-butyl-6,7-dihydro-6-hydroxymethyl-7-oxothiopyrano-[2,3-d]-imidazol-1(5H)-yl]-methyl]-N-[(dimethylamino)-methylene]-(1,1'-biphenyl)-2-sulfonamide
1) Preparation of the organomagnesium compound 600 mg of magnesium turnings and a small amount of mercuric chloride were mixed together under an inert atmosphere and the mixture was stirred for 5 minutes. 2 ml of tetrahydrofuran and 0.1 ml of chloromethyl benzyl ether were added and the reaction medium was heated to 40°-45° C. After cooling to 0°-5° C., 2.8 ml of chloromethyl benzyl ether and 20 ml of tetrahydrofuran were added over one hour followed by stirring for 16 hours at 0°-5° C. A 0.2M/l solution was obtained which was used as is.
2) Condensation 20 ml of the solution of organomagnesium compound prepared above were cooled under inert atmosphere to -30° C. and 280 mg of the product of Stage 6 of Example 1 in 10 ml of tetrahydrofuran were added over 10 minutes. The reaction medium was stirred for 96 hours at 0° C., poured into a saturated aqueous solution of ammonium chloride, extracted with ethyl acetate, washed with salt water and dried. The solvent was evaporated and the residue was chromatographed on silica (eluant: $CH_2Cl_2$-acetone 8-2) to obtain 52 mg of the expected product.

IR Spectrum, $CHCl_3$ Absorption OH+associated 3615 $cm^{-1}$ N=CH—N: 1738, 1680 $cm^{-1}$

EXAMPLE 30

Using the procedure of the preceding examples, the following product was prepared:

2-butyl-1-[[2'-[[(ethoxycarbonyl]-amino]-sulfonyl]-(1,1'-biphenyl)-4-yl]-methyl]-1,5,6,7-tetrahydrothiopyrano-[2,3-d]-imidazol-7-carboxylic acid.

Using the procedure of the preceding examples, 2-butyl-1,5-dihydrothiopyrano-[2,3-d]-imidazol-7-carbonitrile was reacted and the products corresponding to Example 1, 2, 3 and 4 containing a 7-carbonitrile were obtained.

Preparation of 2-butyl-1,5-dihydrothiopyrano-[2,3d]-imidazol-7-carbonitrile

A suspension of 300 mg of the product of Stage 5 of Example 1, 30 ml of toluene, 0.38 ml of trimethylsilylcyanide and 32 mg of zinc iodide was stirred at 60° C. and after 16 hours of stirring at 60° C., the addition of the same quantity of silylated reagent and zinc iodide was carried out. Then after 24 hours of stirring at 60° C., stirring was continued at 60° C. for another 48 hours. Then 5 ml of pyridine and 0.77 ml of phosphorus oxychloride were added and stirring was continued at 80° C. for 4 hours. The reaction medium was cooled, poured into 50 ml of water, extracted with ethyl acetate, washed with a salt solution and dried. The solvent was evaporated under reduced pressure and the residue was chromatographed on silica (eluant: dichloromethane-ethyl acetate 7-3) to obtain 46 mg of the expected product with a $R_f$=0.44 (CHCl$_2$-AcOEt 7-3).

EXAMPLE 31 of Pharmaceutical Composition

Tablets were prepared containing 10 mg of the product of Example 3 and excipient of lactose, talc, starch and magnesium stearate for a tablet weighing 100 mg.

PHARMACOLOGICAL RESULTS

1—Test on the angiotensin II receptor

A fresh membrane preparation obtained from rat's liver was used and the tissue was ground up in a polytron in a 50 mM Tris buffer pH 7.4. The grinding process was followed by 3 centrifugations at 30,000 g for 15 minutes with intermediate taking up of the pellets in the Tris buffer pH 7.4. The last pellets were suspended in an incubation buffer (20 mM Tris, 135 mM NaCl, 10 mM KCl, 5 mM glucose, 10 mM MgCl$_2$, 0.3 mM PMSF, 0.1 mM bacitracin, 0.2% BSA, 2 ml aliquoted fractions were distributed in hemolysis tubes and 125I angiotensin II (25,000 DPM/tube) and the product under test were added. The product was first tested at $3 \times 10^{-5}$M three times. When the product tested displaced more than 50% of the radioactivity linked specifically to the receptor, it was tested again in a range of 7 concentrations to determine the concentration which inhibited 50% of the radioactivity linked specifically to the receptor. In this way, the 50% inhibiting concentration was determined.

The non-specific bond was determined by the addition of a product of Example 94 of European Patent No. 0,253,310 at $10^{-5}$M (three times). After incubation at 25° C. for 150 minutes, the suspension was put in a water-bath at 0° C. for 5 minutes, filtered under vacuum, rinsed with a Tris pH 7.4 buffer and the radioactivity was counted in the presence of scintillating Triton. The result was expressed directly as a 50% inhibiting concentration (IC$_{50}$), that is to say the concentration of product studied, expressed in mM, necessary to displace 50% of the specific radioactivity fixed to the receptor studied. Results:

| Product of Example | IC$_{50}$ in Nanomoles |
|---|---|
| 3 | 1.3 |
| 4 | 0.2 |
| 7 | 5.3 |

2—Test of the antagonistic activity of angiotensin II in a demedullated rat

Male Sprague Dawley rats weighing 250 to 350 g were anaesthetized by an intraperitoneal injection of sodium pentobarbital (60 mg/kg). The diastolic arterial pressure was recorded with a heparinated catheter (PE50) introduced into the left carotid of the animal and connected to a pressure processor (Gould, Pressure Processor) via a Gould pressure sensor. A catheter was introduced into the right jugular of the animal for the injection of the molecules to be studied. The animal was placed under assisted respiration and a bilateral section of the vagus nerves was carried out. The rat was then demedullated.

After a sufficient period of stabilization, study of the antagonism of the compound vis-a-vis angiotensin II (Hypertensin Ciba) was started in the following way.

1—Three consecutive injections of angiotensin II (0.75 micrograms/kg) spaced 15 minutes apart which allowed a reproducible and stable pressure response to be obtained.

2—While maintaining a periodicity of 15 minutes for the administration of angiotensin II, the molecules to be studied were injected 5 minutes before the angiotension II.

The pressure effects of the angiotensin II in the presence of the antagonist were expressed as a percentage of the pressure effects of the angiotensin II administered alone. The 50% inhibitory dose of the studied effect was thus determined. Each animal was considered as its own control.

Results

| Product of Example | 50% Inhibitory Doses (mg/kg) (venous route) |
|---|---|
| 3 | 0.08 |
| 4 | 0.09 |

Various modifications of the products and method of the invention may be made without departing from the spirit or scope thereof and it is to be understood that the invention is intended to be limited only as defined in the appended claims.

What we claim:

1. A compound selected from the group consisting of the formula

41

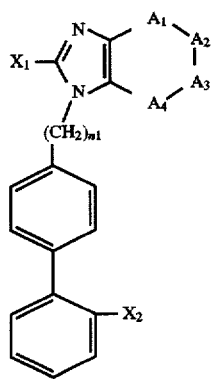

I wherein $X_1$ is selected from the group consisting of an optionally substituted alkyl, alkenyl, alkynyl, alkoxy and alkylthio of up to 6 carbon atoms, which may be interrupted by at least one heteroatom selected from the group consisting of oxygen, nitrogen and sulfur, $n_1$ is an integer from 0 to 4, $A_1$ is optionally oxidized sulfur in a 6-membered ring, $A_2$, $A_3$ and $A_4$ are individually selected from the group consisting of —$(CH_2)_n$—, —CH= and >C=$R_3$, n is an integer from 1 to 2, at least one of the hydrogens of —$(CH_2)_n$— and —CH= are optionally replaced by one or two identical or different $R_1$, and $R_2$ which are selected from the group consisting of halogen, hydroxyl, free, salified or esterified carboxy, acyl, mercapto, amino and acyl-amino in which the amino is optionally substituted by one or two alkyl, alkyl, alkenyl, alkoxy and alkylthio of up to 6 carbon atoms and optionally substituted, phenyl, benzyl, phenethyl and phenoxy in which the phenyl is optionally substituted, =$R_3$ is selected from the group consisting of oxygen, =CH—COOH, optionally substituted alkenyl and =N—$OR_4$, $R_4$ is selected from the group consisting of hydrogen, optionally substituted alkyl, alkenyl, acyl and carbamoyl, $X_2$ is selected from the group consisting of cyano, free, salified or esterified carboxy, tetrazolyl optionally salified or esterified, —$SO_2$—$NH_2$, —$SO_3R_7$ in which $R_7$ is hydrogen or alkyl of 1 to 6 carbon atoms, —NH—$(CH_2)_{n2}$—SO—$(Z)_{n4}$—$R_5$, in which n2 and n4 individually are 0 to 1, —$(CH_2)_{n2}$—$SO_2$—$(Z)_{n4}$—$R_5$, in which Z is selected from the group consisting of —NH—CO—, —NHCO—O—, —N=CH—N—$R_6$, —NH—CO—NH, and a single bond and $R_5$ and $R_6$ are individually selected from the group consisting of hydrogen, alkyl and alkenyl of up to 6 carbon atoms, and benzyl, and alkyl and alkenyl of up to 6 carbon atoms and optionally substituted; all the alkyl, alkenyl, alkoxy, alkylthio, phenyl benzyl, phenethyl and phenoxy being unsubstituted or substituted with at least one member of the group consisting of halogen, hydroxy, nitro, alkyl, alkenyl and alkoxy of up to 4 carbon atoms, trifluoromethyl, cyano, amino, mono and dialkylamino, free, salified or esterified carboxy, phenyl, pyridyl and tetrazolyl; the products of Formula I being in all possible racemic, enantiomeric and diastereoisomeric isomer forms, or their non-toxic, pharmaceutically acceptable salts with acids or bases.

42

2. A compound of formula

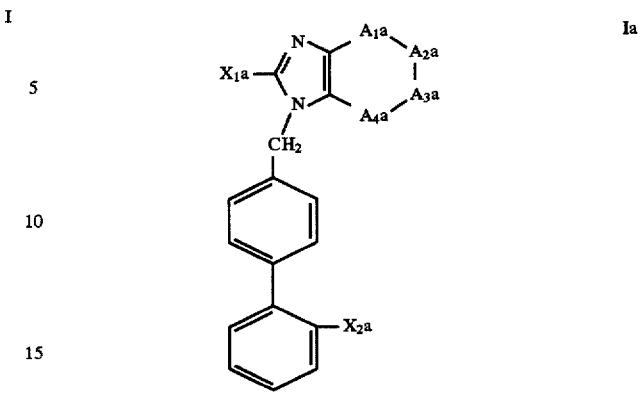

Ia wherein $X_1a$ is alkyl of 1 to 6 carbon atoms, $A_1a$ is optionally oxidized sulfur, $A_2a$ $A_3a$ and $R_1$ are individually selected from the group consisting of —$(CH_2)_{n1a}$— and —CH=, n1a is 1 or 2, one or more of the hydrogens of —$(CH_2)_{n1a}$— and CH= are optionally substituted by one or two $R_1a$ and $R_2a$ selected from the group consisting of halogen, hydroxyl, free, salified or esterified carboxy, amino, mono- and dialkylamino, alkyl, alkoxy and alkylthio of up to 6'carbon atoms, $X_{2a}$ is selected from the group consisting of cyano, free, salified or esterified carboxy, optionally salified or esterified tetrazolyl, —$SO_2$—$NH_2$, —$SO_3R_7$ in which $R_7$ is hydrogen or alkyl of 1 to 6 carbon atoms, —NH—$(CH_2)_{n2}$—$SO_2$—$(Z)_{n1}$—$R_5a$ in which Z is selected from the group consisting of —NH—CO—, —NH—=CO—O—, —N=CH=N—$R_6a$, —NH—CO—NH— and a single bond and $R_5a$ and $R_6a$ are individually selected from the group consisting of hydrogen, methyl, ethyl, propyl, vinyl, alkyl, phenyl, benzyl, and trifluoromethyl, the said products of formula Ia being in all possible racemic, enantiomeric and diastereoisomeric isomer forms or their non-toxic, pharmaceutically acceptable salts with acids or bases.

3. A compound or claim 1 having the formula

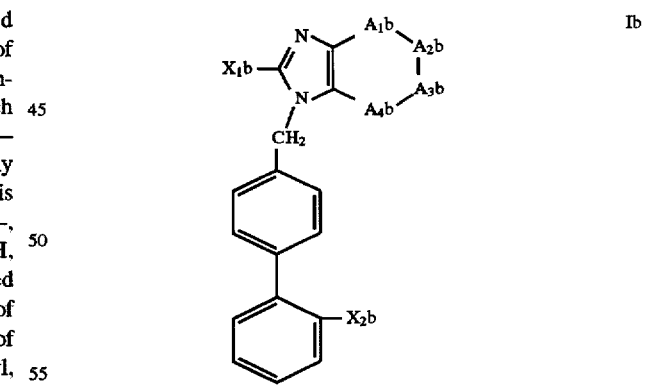

Ib wherein $X_1b$ is selected from the group consisting of methyl, ethyl, propyl, n-butyl, i-butyl or tert-butyl, $A_1b$ is —S—, $A_2b$ is —$(CH_2)_{n1b}$— with n1b being 1 with one or both of the hydrogens optionally substituted by one or two alkyl of 1 to 4 carbon atoms optionally substituted by halogen, hydroxyl, formyl, free, salified or esterified carboxy, $A_3b$ is selected from the group consisting of —$CH_2$— and —CH= with a hydrogen being optionally substituted by halogen, formyl, formyl or free, salified or esterified carboxy, —NH—, —N= and >=O,

43

A₄b is \C=R³ and R³ is selected from the group consisting of [>C=O, >C=N—O—CH₂—COOH, >C=N—OH, >C=CH=COOH, >C=N—O=C—NH—nPr,
     ‖
     O —N=, —NH—, =CH₂— and —CH= with one or both of the hydrogen atoms optionally substituted by one or two individual members of the group consisting of amino, one or two individual members of the group consisting of amino, free salified or esterified carboxy, hydroxyl and halogen,] oxygen, =CH—COOH, optionally substituted alkenyl and =NH—OR₄, R₄ is selected from the group consisting of hydrogen, optionally substituted alkyl, alkenyl, acyl and carbamoyl, X₂b is selected from the group consisting of optionally salified or esterified tetrazolyl, —SO₂—NH₂, —SO₂—NH—CO—O—R₅b, and —SO₂—N=CH—NR₆b, —SO₂—NH —CO—R₅b, and —SO₂—NH—CO—NH—R₅b in which R₅b and R₆b are individually selected from the group consisting of hydrogen, methyl, ethyl, and n-propyl, the said products of formula Ib being in all possible racemic, enantiomeric and diastereoisomeric isomer forms or their non-their non-toxic, pharmaceutically acceptable addition salts with acids or bases.

4. A compound of claim 1 selected from the group consisting of

4'-[(2-butyl-7-oxo-1,5,6,7-tetrahydro-thiopyrano[2,3-d]-imidazol-1-yl)-methyl]-N-[(dimethylamino)-methylene)-(1,1'-biphenyl)-2-sulfonamide, 4'-[(2-butyl-7-oxo-1,5,6,7-tetrahydro-thiopyrano[2,3-d]-imidazol-1-yl)-methyl]-(1,1'-biphenyl)-2-sulfonamide, ethyl (2-(4'-((2-butyl-1,5,6,7-tetrahydro-7-oxo-thiopyrano[2,3-d]-imidazol-1-yl)-methyl)-(1,1'-biphenyl)-sulfonyl)-carbamate, N-(2-(4'-((2-butyl-1,5,6,7-tetrahydro-7-oxo-thiopyrano[2,3-d]imidazol-1-yl)-methyl)-(1,1'-biphenyl)-sulfonyl)-N'-propylurea, 4'-[(2-butyl-7-(hydroxyimino)-1,5,6,7-tetrahydro-thiopyrano-[2,3-d]-imidazol-1-yl)-methyl]-(1,1'-biphenyl)-2-sulfonamide, 4'-[(2-butyl-7-((((propylamino) carbonyl)-oxy)-imino)-1,5,6,7-tetrahydro-thiopyrano[2,3-d]-imidazol-1-yl)-methyl]-N-[(propylamino)-carbonyl]-(1,1'-biphenyl)-2-sulfonamide, 4'[(2-butyl-7-(hydroxyimino)-1,5,6,7-tetrahydro-thiopyrano-[2,3-d]-imidazol-1-yl)-methyl]-N-((propylamino)-carbonyl-(1,1'-biphenyl)-2-sulfonamide, 4'-[(2-butyl-1,7-dihydro-7-oxo-thiopyrano[2,3-d]-imidazol-1-yl)-methyl]-N-[(dimethylamino)-methylene)-(1,1'-biphenyl)-2-sulfonamide, 4'[(2-butyl-1,7-dihydro-7-oxo-thiopyrano[2,3-d]-imidazol-1-yl)-methyl]-(1,1'-biphenyl)-2-sulfonamide and 4'[(2-butyl-1,7-dihydro-7-oxo-thiopyrano[2,3-d]-imidazol-1-yl)-methyl-N-[(propylamino)-carbonyl]-(1,1'-biphenyl)-2-sulfonamide.

5. A composition for inhibiting the effects of angiotensin II comprising an effective amount of a compound of claim sufficient to inhibit the effect of angiotensin II and a pharmaceutical carrier.

6. A composition of claim 5 wherein the active ingredient is selected from the group consisting of:

44

4'-[(2-butyl-7-oxo-1,5,6,7-tetrahydro-thiopyrano[2,3-d]-imidazol-1-yl)-methyl]-N-[(dimethylamino)-methylene)-(1,1,-biphenyl)- 2-sulfonamide, 4'-[(2-butyl-7-oxo-1,5,6,7-tetrahydro-thiopyrano[2,3-d]-imidazol-1-yl)-methyl]-(1,1'-biphenyl)-2-sulfonamide, ethyl (2-(4'-((2-butyl-1,5,6,7-tetrahydro-7-oxo-thiopyrano[2,3-d]-imidazol-1-yl)-methyl)-(1,1'-biphenyl)-sulfonyl)-carbamate, N-(2-(4'-((2-butyl-1,5,6,7-tetrahydro-7-oxo-thiopyrano[2,3-d]imidazol-1-yl)-methyl)-(1,1'-biphenyl)-sulfonyl)-N'-propylurea, 4'-[(2-butyl-7-(hydroxyimino)-1,5,6,7-tetrahydro-thiopyrano-[2,3-d]-imidazol-1-yl)-methyl]-(1,1'-biphenyl)-2-sulfonamide, 4'-[(2-butyl-7-((((propylamino) carbonyl)-oxy)-imino)-1,5,6,7-tetrahydro-thiopyrano[2,3-d]-imidazol-1-yl)-methyl]-N-[(propylamino)-carbonyl]-(1,1'-biphenyl)-2-sulfonamide, 4'[(2-butyl-7-(hydroxyimino)-1,5,6,7-tetrahydro-thiopyrano-[2,3-d]-imidazol-1-yl)-methyl]-N-((propylamino)-carbonyl-(1,1'-biphenyl)-2-sulfonamide, 4'-[(2-butyl-1,7-dihydro-7-oxo-thiopyrano[2,3-d]-imidazol-1-yl)-methyl]-N-[(dimethylamino)-methylene)-(1,1'-biphenyl)-2-sulfonamide, 4'[(2-butyl-1,7-dihydro-7-oxo-thiopyrano[2,3-d]-imidazol-1-yl)-methyl]-(1,1'-biphenyl)-2-sulfonamide and 4'[(2-butyl-1,7-dihydro-7-oxo-thiopyrano[2,3-d]-imidazol-1-yl)-methyl-N-[(propylamino)-carbonyl]-(1,1'-biphenyl)-2-sulfonamide.

7. A method of inhibiting angiotensin II effects in warm-blooded animals comprising administering to warm-blooded animals an amount of a compound of claim 1 sufficient to inhibit angiotensin II effects.

8. A method of claim 7 wherein the active compound is selected from the group consisting of:

4'-[(2-butyl-7-oxo-1,5,6,7-tetrahydro-thiopyrano[2,3-d]-imidazol-1-yl)-methyl]-N-[(dimethylamino)-methylene)-(1,1'-biphenyl)-2-sulfonamide, 4'-[(2-butyl-7-oxo-1,5,6,7-tetrahydro-thiopyrano[2,3-d]-imidazol-1-yl)-methyl]-(1,1'-biphenyl)-2-sulfonamide, ethyl (2-(4'-((2-butyl-1,5,6,7-tetrahydro-7-oxo-thiopyrano[2,3-d]-imidazol-1-yl)-methyl)-(1,1'-biphenyl)-sulfonyl)-carbamate, N-(2-(4'-((2-butyl-1,5,6,7-tetrahydro-7-oxo-thiopyrano[2,3-d]imidazol-1-yl)-methyl)-(1,1'-biphenyl)-sulfonyl)-N'-propylurea, 4'-[(2-butyl-7-(hydroxyimino)-1,5,6,7-tetrahydro-thiopyrano-[2,3-d]-imidazol-1-yl)-methyl]-(1,1'-biphenyl)-2-sulfonamide, 4'-[(2-butyl-7-((((propylamino) carbonyl)-oxy)-imino)-1,5,6,7-tetrahydro-thiopyrano[2,3-d]-imidazol-1-yl)-methyl]-N-[(propylamino)-carbonyl]-(1,1'-biphenyl)-2-sulfonamide, 4'[(2-butyl-7-(hydroxyimino)-1,5,6,7-tetrahydro-thiopyrano-2,3-d]-imidazol-1-yl)-methyl]-N-((propylamino)-carbonyl-(1,1'-biphenyl)-2-sulfonamide, 4'-[(2-butyl-1,7-dihydro-7-oxo-thiopyrano[2,3-d]-imidazol-1-yl)-methyl]-N-[(dimethylamino)-methylene)-(1,1'-biphenyl)-2-sulfonamide, 4'[(2-butyl-1,7-dihydro-7-oxo-thiopyrano[2,3-d]-imidazol-1-yl)-methyl]-(1,1'-biphenyl)-2-sulfonamide and 4'[(2-butyl-1,7-dihydro-7-oxo-thiopyrano[2,3-d]-imidazol-1-yl)-methyl-N-(propylamino)-carbonyl]-(1,1'-biphenyl)-2-sulfonamide.

* * * * *